(12) United States Patent
Kawooya

(10) Patent No.: US 11,312,745 B2
(45) Date of Patent: Apr. 26, 2022

(54) METHODS OF PURIFYING FC-CONTAINING PROTEINS

(71) Applicant: Amgen Inc., Thousand Oaks, CA (US)

(72) Inventor: John K. Kawooya, Moorpark, CA (US)

(73) Assignee: AMGEN INC., Thousand Oaks, CA (US)

(*) Notice: Subject to any disclaimer, the term of this patent is extended or adjusted under 35 U.S.C. 154(b) by 520 days.

(21) Appl. No.: 16/093,994

(22) PCT Filed: Jul. 21, 2017

(86) PCT No.: PCT/US2017/043384
§ 371 (c)(1),
(2) Date: Oct. 16, 2018

(87) PCT Pub. No.: WO2018/018011
PCT Pub. Date: Jan. 25, 2018

(65) Prior Publication Data
US 2019/0127418 A1 May 2, 2019

Related U.S. Application Data

(60) Provisional application No. 62/365,943, filed on Jul. 22, 2016.

(51) Int. Cl.
| | |
|---|---|
| *C07K 1/22* | (2006.01) |
| *B01D 15/34* | (2006.01) |
| *B01D 15/38* | (2006.01) |
| *B01D 15/42* | (2006.01) |
| *C07K 16/00* | (2006.01) |
| *C07K 1/34* | (2006.01) |

(52) U.S. Cl.
CPC .............. *C07K 1/22* (2013.01); *B01D 15/34* (2013.01); *B01D 15/3809* (2013.01); *B01D 15/426* (2013.01); *C07K 1/34* (2013.01); *C07K 16/00* (2013.01); *C07K 2317/31* (2013.01); *C07K 2317/35* (2013.01); *C07K 2317/60* (2013.01); *C07K 2317/622* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,693,181 | B2* | 2/2004 | Ashkenazi | C07K 14/7151 435/69.1 |
| 2010/0130727 | A1* | 5/2010 | Zhou | C07K 1/22 530/387.1 |
| 2010/0168395 | A1 | 7/2010 | Sato | |
| 2010/0256336 | A1* | 10/2010 | Yuk | C12P 21/005 530/387.3 |
| 2011/0144311 | A1* | 6/2011 | Chmielowski | C07K 16/18 530/388.1 |
| 2012/0184711 | A1* | 7/2012 | Sato | C07K 1/22 530/324 |
| 2015/0133640 | A1* | 5/2015 | Blein | C07K 16/2896 530/387.3 |

FOREIGN PATENT DOCUMENTS

| | | |
|---|---|---|
| CN | 102382190 A | 4/2014 |
| WO | 2010151688 A2 | 12/2010 |
| WO | 2011034605 A2 | 3/2011 |
| WO | 2013009526 A1 | 1/2013 |
| WO | 2013147691 A1 | 10/2013 |
| WO | 20144081955 A1 | 5/2014 |

OTHER PUBLICATIONS

Shukla et al. "Strategies to address aggregation during protein A chromatography". pp. 36-44, Nov. 2005 (Year: 2005).*
Koguma et al. "Novel purification method of human immunoglobulin by using a thermo-responsive protein A" J. of Chromatography A. pp. 149-153 (Year: 2013).*
Mueller et al. Liquid formulations for long-term storage of monoclonal IgGs, Appl Biochem Biotechnol 169: 1431-1448 (Year: 2013).*
Chen et al. In vitro folding of methionine-arginine human lyspro-proinsulin S-sulfonate-disulfide formation pathways and factors controlling yeild, Wiley online library, pp. 1332-1343, Jun. 10, 2010. (Year: 2010).*
Agilent Technologies "Size exclusion chromatography for biomolecule analysis" pp. 1-20; copyright 2015. (Year: 2015).*
International Search Report for PCT Application No. PCT/US2017/043384, dated Feb. 2, 2018.
Arakawa, et al; *Elution of antibodies from a Protein-A column by aqueous arginine solutions*; Protein Expression and Purification 36 (2004) 244-248.
Takaluoma, et al; *Lysyl hydroxylase 2 is a specific telopeptide hydroxylase, while all three isoenzymes hydroxylate collagenous sequences*; Matrix Biology 26 (2007) 396-403.
Ejima, et al., *Effective elution of antibodies by arginine and arginine derivatives in affinity column chromatography*, Analytical Biochemistry, v 345; pp. 250-257; 2005.
Chen, et al, *Improved protein-A chromatography for monoclonal antibody purification*, CN J Biotechnology, v 32 (6) pp. 807-818, 2016.

* cited by examiner

*Primary Examiner* — Daniel E Kolker
*Assistant Examiner* — James L Rogers
(74) *Attorney, Agent, or Firm* — Susan E. Lingenfelter

(57) ABSTRACT

The present invention relates to methods of purifying proteins containing Fc regions, such as antibodies and Fc fusion proteins. In particular, the present invention relates to a purification method resulting in reduced levels of aggregate protein comprising adsorbing an Fc region-containing protein to a temperature-responsive protein A resin and eluting the protein from the resin at a temperature below 35 C with an elution buffer comprising a chaotropic agent, a sugar alcohol, and at least one amino acid. Methods of separating fully assembled antibodies from half antibody forms thereof using the elution buffer are also described.

85 Claims, 20 Drawing Sheets
Specification includes a Sequence Listing.

| Peak # | RT (min) | Area | % Area | Height |
|---|---|---|---|---|
| 1 | 2.371 | 118.81806 | 4.1654 | 5.85285 |
| 2 | 2.630 | 200.14401 | 7.0164 | 8.50874 |
| 3 | 3.103 | 2533.56201 | 88.8183 | 205.36591 |

SEQUENCE LISTING

<160> NUMBER OF SEQ ID NOS: 14

<210> SEQ ID NO 1
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 1

Ala Asp Asn Lys Phe Asn Lys Glu Gln Gln Asn Ala Phe Tyr Glu Ile
1               5                   10                  15

Leu His Gly Pro Asn Gly Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 2
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 2

Ala Asp Asn Lys Phe Asn Lys Glu Gln Gln Asn Ala Phe Tyr Glu Ile
1               5                   10                  15

Leu His Ala Pro Asn Gly Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 3
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 3

Ala Asp Asn Lys Phe Asn Lys Glu Gln Gln Asn Ala Phe Tyr Glu Ile
1               5                   10                  15

Leu His Leu Pro Asn Gly Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 4
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 4

Ala Asp Asn Lys Phe Asn Lys Glu Gln Gln Asn Ala Phe Tyr Glu Ile

```
                1               5                  10                  15
Leu His Gly Pro Asn Ala Asn Glu Glu Gln Arg Asn Ala Phe Ile Gln
                    20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 5
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 5

Ala Asp Asn Lys Phe Asn Lys Glu Gln Gln Asn Ala Phe Tyr Glu Ile
1               5                  10                  15

Leu His Gly Pro Asn Leu Asn Glu Glu Gln Arg Asn Ala Phe Ile Gln
                    20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 6
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 6

Ala Asp Asn Lys Phe Asn Lys Glu Gln Gln Asn Ala Phe Tyr Glu Ile
1               5                  10                  15

Leu His Ala Pro Asn Ala Asn Glu Glu Gln Arg Asn Ala Phe Ile Gln
                    20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 7
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 7

Ala Asp Asn Lys Phe Asn Lys Glu Gln Gln Asn Ala Phe Tyr Glu Ile
1               5                  10                  15

Leu His Leu Pro Asn Gly Asn Glu Glu Gln Arg Asn Ala Ala Ile Gln
                    20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 8
```

```
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 8

Ala Asp Asn Lys Phe Asn Lys Glu Gln Gln Asn Ala Phe Tyr Glu Ile
1               5                   10                  15

Leu His Leu Pro Asn Gly Asn Glu Glu Gln Arg Asn Ala Gly Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 9
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 9

Ala Asp Asn Lys Phe Asn Lys Glu Gln Gln Asn Ala Phe Tyr Glu Ile
1               5                   10                  15

Leu His Leu Pro Asn Gly Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Gly Asn Asp Ala Gln Ala Pro Lys Ala
    50                  55

<210> SEQ ID NO 10
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 10

Ala Asp Asn Lys Glu Asn Lys Glu Gln Gln Asn Ala Phe Tyr Glu Ile
1               5                   10                  15

Leu His Leu Pro Asn Gly Asn Glu Glu Gly Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Ala
    50                  55

<210> SEQ ID NO 11
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 11

Ala Asp Asn Lys Phe Asn Lys Glu Gln Gln Asn Ala Phe Tyr Glu Thr
1               5                   10                  15

Leu His Leu Pro Asn Gly Asn Glu Glu Gln Gly Asn Ala Phe Ile Gln
            20                  25                  30
```

-continued

Ser Leu Lys Asp Asp Pro Ser Gln Ser Ala Asn Leu Leu Ala Glu Ala
         35                  40                  45

Lys Lys Leu Asn Asp Ala Gln Ala Pro Lys Ala
     50                  55

<210> SEQ ID NO 12
<211> LENGTH: 59
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (7)..(7)
<223> OTHER INFORMATION: Xaa can be any naturally occurring amino acid

<400> SEQUENCE: 12

Ala Asp Asn Lys Phe Asn Xaa Glu Gln Gln Asn Ala Phe Tyr Glu Ile
1               5                   10                  15

Leu His Gly Pro Asn Ala Asn Glu Glu Gln Arg Asn Ala Gly Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys Ala
     50                  55

<210> SEQ ID NO 13
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 13

Ala Asp Asn Lys Glu Asn Lys Glu Gln Gln Asn Ala Phe Tyr Glu Ile
1               5                   10                  15

Leu His Gly Pro Asn Ala Asn Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Gly Asn Asp Ala Gln Ala Pro Lys Ala
     50                  55

<210> SEQ ID NO 14
<211> LENGTH: 59
<212> TYPE: PRT
<213> ORGANISM: Artificial Sequence
<220> FEATURE:
<223> OTHER INFORMATION: Synthetic polypeptide

<400> SEQUENCE: 14

Ala Asp Asn Lys Phe Asn Lys Glu Gln Gln Asn Ala Phe Tyr Glu Ile
1               5                   10                  15

Leu His Gly Pro Asn Ala Thr Glu Glu Gln Arg Asn Ala Phe Ile Gln
             20                  25                  30

Ser Leu Lys Asp Asp Pro Ser Gln Ser Ala Asn Leu Leu Ala Glu Ala
         35                  40                  45

Lys Lys Leu Asn Asp Ala Gln Ala Pro Lys Ala
     50                  55

METHODS OF PURIFYING FC-CONTAINING PROTEINS

CROSS-REFERENCE TO RELATED APPLICATIONS

This application claims the benefit of U.S. Provisional Application No. 62/365,943, filed Jul. 22, 2016, which is hereby incorporated by reference in its entirety.

DESCRIPTION OF THE TEXT FILE SUBMITTED ELECTRONICALLY

The present application contains a Sequence Listing, which has been submitted electronically in ASCII format and is hereby incorporated by reference in its entirety. The computer readable format copy of the Sequence Listing, which was created on Jul. 20, 2017, is named A-2036-WO-PCT_SeqList_ST25 and is 8.81 kilobytes in size.

FIELD OF THE INVENTION

The present invention relates to the field of biopharmaceutical manufacturing. In particular, the invention relates to methods for reducing or preventing aggregation of Fc region-containing proteins during purification operations. The invention also relates to methods of separating antibodies from difficult to remove contaminants, such as half antibodies.

BACKGROUND OF THE INVENTION

Aggregation remains a major issue in production of genetically engineered biologics, particularly fusion proteins comprising immunoglobulin Fc regions, such as multispecific antigen binding proteins. Protein aggregates are unacceptable in therapeutic drugs due to their severe immunogenicity (Maggio, Journal of Excipients and Food Chemicals, Vol. 3 (2): 45-53, 2012; Sauerborn et al., Trends Pharmacol. Sci., Vol. 31(2): 53-59, 2010). Protein aggregation can occur during recombinant expression of the protein as a result of the vigorous shaking of the cell culture required for sufficient aeration of the media (Vazquez-Rey and Lang, Biotechnology and Bioengineering, Vol. 108(7): 1494-1508, 2011). In addition, many proteins are prone to unfolding, followed by aggregation upon exposure to extreme pH conditions (i.e. pH>9.0 or pH<4.5). The typical method for purifying proteins comprising immunoglobulin Fc regions entails capture of the proteins with a protein A affinity resin and subsequent elution from the resin with a low pH, acidic buffer (e.g. pH 2.7 to 3.7) (Hari et al., Biochemistry, Vol. 49(43): 9328-9338, 2010; Ejima et al., PROTEINS: Structure, Function, and Bioinformatics, Vol. 66:954-962, 2007). The low pH elution does not only induce aggregation of the proteins resulting in reduced yields, but may also compromise the long-term stability of the recovered non-aggregated proteins.

In an attempt to avoid the undesirable effects of the low pH elution from protein A resins, a temperature-responsive protein A resin was developed as an alternative to conventional protein A resins. This new resin is comprised of a mutant version of protein A that binds to the Fc region of immunoglobulins at temperatures below 10° C., but loses affinity for the Fc region at elevated temperatures (e.g. 40° C.) (Koguma et al., Journal of Chromatography A, Vol. 1305: 149-153, 2013). The temperature-responsive protein A resin was initially received with great enthusiasm because it allows the elution of Fc region-containing proteins from the resin at neutral pH by simply heating the column (Koguma et al., Journal of Chromatography A, Vol. 1305: 149-153, 2013). Although purification of proteins with the temperature-responsive protein A resin produces stable molecules, the approach is impractical because it requires a shift of 30° or more of the column temperature from column loading to elution, thus creating a significant lag time between the loading and elution steps. The time delay required to manipulate column temperature adds a tremendous amount of cycle time to purification operations, thereby making this approach undesirable for both large scale manufacturing processes and high-throughput purification of large panels of proteins during the discovery phase. Moreover, the impact of large temperature swings on the stability of proteins eluted from the temperature-responsive protein A resin remains unknown.

Accordingly, there is a need in the art for efficient purification methods for Fc region-containing proteins that minimize or reduce the effects on the structural integrity of the proteins associated with the prior protein A chromatography methods.

SUMMARY OF THE INVENTION

The present invention is based, in part, on the development of a buffer composition that allows the elution of a bound Fc region-containing protein from a temperature-responsive protein A resin at neutral pH and constant temperature. A purification scheme employing a temperature-responsive protein A resin in combination with the elution buffers described herein results in reduced levels of aggregated protein, thereby reducing the number of downstream purification steps. Additionally, such purification methods are readily scalable for industrial manufacturing because elution with the elution buffers described herein can be conducted in a temperature-independent manner.

Accordingly, the present invention provides a method for purifying a protein comprising an Fc region. In one embodiment, the method comprises contacting a solution comprising the protein and one or more impurities with a temperature-responsive protein A material at a temperature at which the protein binds to the material; and eluting the protein from the material at a temperature below about 35° C. with an elution buffer described herein, wherein the protein is purified from one or more impurities in the solution.

In certain embodiments, the present invention also provides a method for reducing aggregation during purification of a protein comprising an Fc region. In one embodiment, the method comprises adsorbing the protein to a temperature-responsive protein A material at a temperature at which the protein binds to the material; and eluting the protein from the material at a temperature below about 35° C. with an elution buffer described herein, wherein the amount of the Fc region-containing protein in aggregated form in the eluate is less than the amount in an eluate from a conventional protein A material. In some embodiments, the amount of the Fc region-containing protein in aggregated form in the eluate from the temperature-responsive protein A material is less than 30%. In related embodiments, at least 70% of the Fc region-containing protein in the eluate from the temperature-responsive protein A material is in monomeric form.

The elution buffers employed in the methods of the invention have a pH in the neutral range (e.g. pH of about 6.5 to about 7.5) and comprise a chaotropic agent and a sugar alcohol. In some embodiments, the chaotropic agent and sugar alcohol are present in a molar concentration ratio of about 0.4 to about 4.5. In one embodiment, the molar concentration ratio of the chaotropic agent to sugar alcohol is about 1.1 to about 1.8. The concentration of the chaotropic agent in the elution buffer may be from about 0.4 M to about 5 M depending on the particular chaotropic agent used. In some embodiments, the chaotropic agent may be urea, guanidinium chloride, or a thiocyanate salt (e.g. sodium thiocyanate, potassium thiocyanate, or ammonium thiocyanate). In certain embodiments, the chaotropic agent is urea. In other embodiments, the chaotropic agent is guanidinium chloride. The concentration of the sugar alcohol in the elution buffer may be from about 1 M to about 4.5 M. In certain embodiments, the sugar alcohol is sorbitol, mannitol, xylitol, or glycerol. In one embodiment, the sugar alcohol is sorbitol. In another embodiment, the sugar alcohol is mannitol.

In some embodiments, the elution buffer employed in the methods of the invention further comprises one or more amino acids. The amino acids can be apolar amino acids, such as alanine, cysteine, glycine, isoleucine, leucine, methionine, phenylalanine, proline, tryptophan, or valine, and/or basic amino acids, such as histidine, lysine, ornithine, or arginine. In certain embodiments, the elution buffer comprises at least one apolar amino acid and at least one basic amino acid. For instance, in one embodiment, the elution buffer comprises proline and arginine. The concentration of the amino acids in the elution buffer can be from about 0.25 M to about 1 M.

In various embodiments, the elution buffer may further comprise a salt, such as a sodium salt or chloride salt. The salt may be present in the elution buffer at a concentration of about 0.1 M to about 1 M. In some embodiments, the salt included in the elution buffer is sodium chloride.

In certain embodiments, the elution buffer used in the methods of the invention comprises about 2 M to about 4.5 M of a chaotropic agent, about 1 M to about 4.5 M of a sugar alcohol, about 0.25 M to about 1 M of a basic amino acid, about 0.25 M to about 1 M of an apolar amino acid, and about 0.25 M to about 0.8 M of a salt. In some such embodiments, the chaotropic agent is urea, the sugar alcohol is sorbitol, the basic amino acid is arginine, the apolar amino acid is proline, and the salt is sodium chloride.

Elution of the Fc region-containing protein from the temperature-responsive protein A material according to the methods of the invention can be performed at a temperature from about 1° C. to about 25° C. In some embodiments, elution of the protein is performed at the same or similar temperature at which the protein was adsorbed or bound to the temperature-responsive protein A material. For instance, in one embodiment, elution of the Fc region-containing protein is performed at a temperature less than about 10° C., e.g. from about 1° C. to about 6° C. In other embodiments, elution of the Fc region-containing protein is performed at room temperature, for example at about 20° C. to about 25° C.

Fc region-containing proteins that can be purified according to the methods described herein include antibodies, Fc-fusion proteins, and multi-specific antigen binding proteins. In some embodiments, the Fc region-containing protein is an antibody. In other embodiments, the Fc region-containing protein is an Fc-fusion protein, such as an Fc-fusion protein comprising at least one single chain Fv fragment. The Fc region-containing proteins can be produced recombinantly, for example in mammalian cells. In such embodiments, the Fc region-containing proteins can be purified from cell culture supernatants or cell lysates, such as those produced as a result of harvest operations from a bioreactor.

The invention is also based, in part, on the discovery that size exclusion chromatography, when used with a buffer comprising a chaotropic agent, a sugar alcohol, and at least one amino acid as the mobile phase, can effectively separate fully assembled antibodies from half antibody contaminants. Accordingly, the present invention also provides a method for separating antibodies from half antibody forms thereof. In one embodiment, the method comprises contacting a solution comprising antibodies and half antibody forms thereof with a gel filtration matrix using a mobile phase having a pH of about 6.5 to about 7.5 and comprising a chaotropic agent, a sugar alcohol, an apolar amino acid, and a basic amino acid; and collecting elution fractions from the gel filtration matrix, wherein the antibodies are eluted in one set of elution fractions and the half antibody forms thereof are eluted in another set of elution fractions, thereby separating the antibodies from the half antibody forms thereof. In certain embodiments of the method, the antibodies are multispecific (e.g. bispecific) heterodimeric antibodies.

Any of the elution buffers described herein for eluting Fc region-containing proteins from a temperature-responsive protein A resin at neutral pH and constant temperature can be used as a mobile phase in size exclusion chromatography for separating antibodies from half antibody forms thereof. In some embodiments, the mobile phase comprises about 2 M to about 4.5 M of a chaotropic agent, about 1 M to about 4.5 M of a sugar alcohol, about 0.25 M to about 1 M of a basic amino acid, and about 0.25 M to about 1 M of an apolar amino acid. In these and other embodiments, the mobile phase comprises urea, sorbitol, arginine, and proline. In certain embodiments, the mobile phase comprises about 2 M to about 4.5 M urea, about 1 M to about 4.5 M sorbitol, about 0.25 M to about 1 M arginine, about 0.25 M to about 1 M proline, and 0.25 M to about 0.8 M sodium chloride. In some embodiments, the mobile phase comprises about 4 M urea, about 2.2 M sorbitol, about 0.5 M arginine, about 0.5 M proline, and about 0.75 M sodium chloride. The pH of the mobile phase may be from about 6.5 to about 7.5 or in particular embodiments, from about 7.0 to about 7.4.

In certain embodiments of the method, the mobile phase is passed through the gel filtration matrix at a flow rate of about 0.01 ml/min to about 0.2 ml/min. In other embodiments, the mobile phase is passed through the gel filtration matrix at a flow rate of about 0.02 ml/min to about 0.06 ml/min. The gel filtration matrix may be comprised of cross-linked agarose and dextran and can have a fractionation range of about 10 kDa to about 600 kDa.

DETAILED DESCRIPTION

Figure 1:
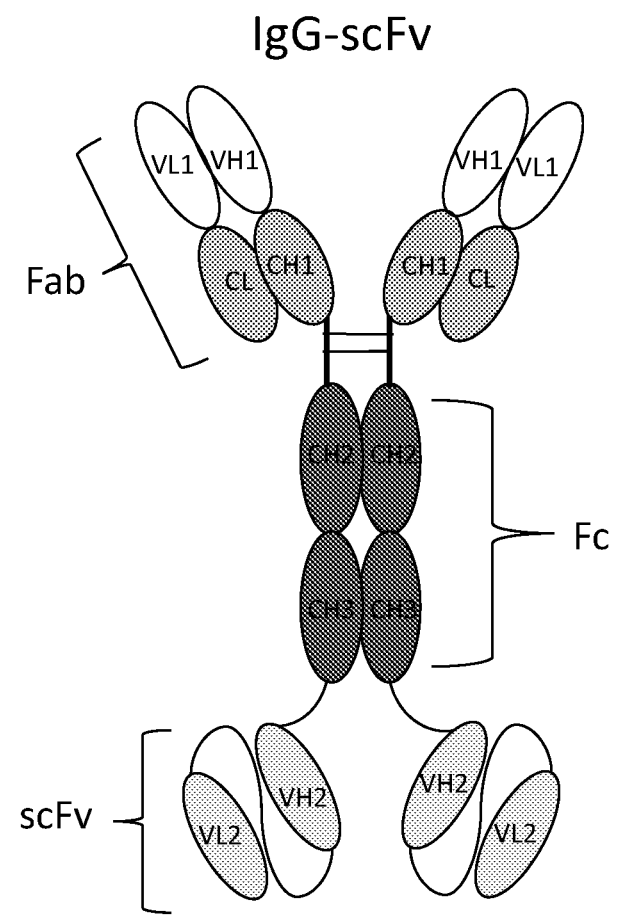
FIG. 1. Structure of IgG-scFv binding protein. The figure depicts a schematic representation of an IgG-scFv binding protein, an example of an Fc-containing protein that can be purified by the methods described herein. An IgG-scFv binding protein is comprised of two single-chain variable fragments (scFvs), each of which comprises variable domains from a first antibody linked together by a peptide linker, fused to the carboxyl-termini of the heavy chains of a second antibody through another peptide linker.

The present invention is based, in part, on the development of a purification procedure for proteins containing an Fc region (e.g. antibodies and Fc fusion proteins) that minimizes levels of aggregated protein and other contaminants, such as half antibodies. Conventional methods for purifying Fc region-containing proteins typically employ protein A affinity chromatography columns, which require extremely acidic solutions to elute bound proteins from the column. Such acidic solutions often induce aggregation, instability, and often precipitation of the proteins. Although modified temperature-responsive protein A resins, which allow for elution of bound proteins at neutral pH using a temperature shift, have been developed, such modified resins are not amenable to large-scale manufacturing operations due to the significant time required to elevate the temperature of the resins.

The inventor has devised a purification method for Fc region-containing proteins that avoids the use of low pH elution buffers of traditional protein A chromatography and the elevated temperatures required for the modified temperature-responsive protein A resins. The purification methods of the invention employ an elution buffer comprising a chaotropic agent, a sugar alcohol, and optionally one or more amino acids. The composition of the elution buffer allows for proteins bound to a temperature-responsive protein A resin to be removed or eluted from the resin at a neutral pH without elevating the temperature of the resin above 35° C. It has also been surprisingly found that this elution buffer can also be used as a mobile phase in size exclusion chromatography to efficiently separate antibodies from half antibody forms thereof.

Thus, in one embodiment, the present invention provides a method for purifying a protein comprising an Fc region from a solution comprising the protein and one or more impurities, the method comprising contacting the solution with a temperature-responsive protein A material at a temperature at which the protein binds to the material; and eluting the protein from the material at a temperature below about 35° C. with an elution buffer described herein.

In another embodiment, the present invention provides a method for separating antibodies from half antibody forms thereof comprising contacting a solution comprising antibodies and half antibody forms thereof with a gel filtration matrix using as a mobile phase one of the elution buffers described herein, and collecting elution fractions from the gel filtration matrix, wherein the antibodies are eluted in one set of elution fractions and the half antibody forms thereof are eluted in another set of elution fractions, thereby separating the antibodies from the half antibody forms thereof.

The methods of the invention are particularly suitable for purifying proteins comprising an immunoglobulin Fc region. As used herein, a "protein comprising an Fc region" or an "Fc region-containing protein" refers to a protein or polypeptide comprising a consecutive amino acid sequence corresponding to the amino acid sequence of an immunoglobulin Fc region. The term "Fe region" refers to the C-terminal region of an immunoglobulin heavy chain, which may be generated by papain digestion of an intact antibody. The Fc region of an immunoglobulin generally comprises two constant domains, a CH2 domain and a CH3 domain, and optionally comprises a CH4 domain. In certain embodiments, the Fc region is an Fc region from an IgG1, IgG2, IgG3, or IgG4 immunoglobulin. In some embodiments, the Fc region comprises CH2 and CH3 domains from a human IgG1 or human IgG2 immunoglobulin.

Fc region-containing proteins that may be purified according to the methods of the invention include, but are not limited to, antibodies, Fc-fusion proteins, and multi-specific antigen binding proteins. As used herein, the term "antibody" refers to a tetrameric immunoglobulin protein comprising two light chain polypeptides (about 25 kDa each) and two heavy chain polypeptides (about 50-70 kDa each). The term "light chain" or "immunoglobulin light chain" refers to a polypeptide comprising, from amino terminus to carboxyl terminus, a single immunoglobulin light chain variable region (VL) and a single immunoglobulin light chain constant domain (CL). The immunoglobulin light chain constant domain (CL) can be kappa (κ) or lambda (λ). The term "heavy chain" or "immunoglobulin heavy chain" refers to a polypeptide comprising, from amino terminus to carboxyl terminus, a single immunoglobulin heavy chain variable region (VH), an immunoglobulin heavy chain constant domain 1 (CH1), an immunoglobulin hinge region, an immunoglobulin heavy chain constant domain 2 (CH2), an immunoglobulin heavy chain constant domain 3 (CH3), and optionally an immunoglobulin heavy chain constant domain 4 (CH4). Heavy chains are classified as mu (μ), delta (Δ), gamma (γ), alpha (α), and epsilon (ε), and define the antibody's isotype as IgM, IgD, IgG, IgA, and IgE, respectively. The IgG-class and IgA-class antibodies are further divided into subclasses, namely, IgG1, IgG2, IgG3, and IgG4, and IgA1 and IgA2, respectively. The heavy chains in IgG, IgA, and IgD antibodies have three domains (CH1, CH2, and CH3), whereas the heavy chains in IgM and IgE antibodies have four domains (CH1, CH2, CH3, and CH4). The immunoglobulin heavy chain constant domains can be from any immunoglobulin isotype, including subtypes. The antibody chains are linked together via inter-polypeptide disulfide bonds between the CL domain and the CH1 domain (i.e. between the light and heavy chain) and between the hinge regions of the antibody heavy chains.

Antibodies that may be purified according to the methods of the invention include, but are not limited to, polyclonal antibodies, monoclonal antibodies, recombinant antibodies, chimeric antibodies, humanized antibodies, and human antibodies. In some embodiments, the antibodies are acid-sensitive antibodies. As used herein, "acid-sensitive antibodies" refer to antibodies that are unstable, aggregate, or lose structural integrity at acidic conditions (e.g. at pH lower than about 6). In certain embodiments, the antibodies are multi-specific (e.g. bispecific) heterodimeric antibodies. Multi-specific heterodimeric antibodies refer to antibodies that are capable of specifically binding to two or more different antigens and comprise two different light chains and two different heavy chains. For instance, in some embodiments, a bispecific heterodimeric antibody comprises a light chain and heavy chain from a first antibody that specifically binds to a first antigen and a light chain and heavy chain from a second antibody that specifically binds to a second antigen (see schematic on the right side of FIGS. 9A and 9B, where the filled symbols represent a light and heavy chain that form a binding site to a first antigen and the non-filled symbols represent a light and heavy chain that form a binding site to a second antigen). Bispecific heterodimeric antibodies can be produced by co-expressing the two light chains and two heavy chains in the same cell or expressing the polypeptide chains separately and subsequently assembling them. To promote heterodimer formation, the polypeptide chains can be engineered using, for example, a "knobs-into-holes" method or charge pairing method. Such methods are known to those of skill in the art and are described in WO 96/027011; Ridgway et al., Protein Eng., Vol. 9: 617-621, 1996; Merchant et al., Nat, Biotechnol., Vol. 16: 677-681, 1998; WO 2009/089004; WO 2014/081955; and Gunasekaran et al., J. Biol. Chem., Vol. 285: 19637-19646, 2010, all of which are hereby incorporated by reference in their entireties.

In certain embodiments, the antibodies to be purified according to the methods of the invention are monoclonal antibodies. The term "monoclonal antibody" (or "mAb") as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against an individual antigenic site or epitope, in contrast to polyclonal antibody preparations that typically include different antibodies directed against different epitopes. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In some embodiments, the monoclonal antibodies may be humanized antibodies. A "humanized antibody" refers to an antibody in which regions (e.g. framework regions) have been modified to comprise corresponding regions from a human immunoglobulin. Generally, a humanized antibody can be produced from a monoclonal antibody raised initially in a non-human animal. Certain amino acid residues in this monoclonal antibody, typically from non-antigen recognizing portions of the antibody, are modified to be homologous to corresponding residues in a human antibody of corresponding isotype. Humanization can be performed, for example, using various methods by substituting at least a portion of a rodent variable region for the corresponding regions of a human antibody (see, e.g., U.S. Pat. Nos. 5,585,089 and 5,693,762; Jones et al., Nature, Vol. 321:522-525, 1986; Riechmann et al., Nature, Vol. 332:323-27, 1988; Verhoeyen et al., Science, Vol. 239:1534-1536, 1988). The CDRs of light and heavy chain variable regions of antibodies generated in another species can be grafted to consensus human framework regions (FRs). To create consensus human FRs, FRs from several human heavy chain or light chain amino acid sequences may be aligned to identify a consensus amino acid sequence.

In other embodiments, the monoclonal antibodies may be fully human antibodies. A "fully human antibody" is an antibody that comprises variable and constant regions derived from or indicative of human germ line immunoglobulin sequences. Fully human antibodies can be produced by immunizing transgenic animals (usually mice) that are capable of producing a repertoire of human antibodies in the absence of endogenous immunoglobulin production. Antigens for this purpose typically have six or more contiguous amino acids, and optionally are conjugated to a carrier, such as a hapten. See, e.g., Jakobovits et al., 1993, *Proc. Natl. Acad. Sci. USA* 90:2551-2555; Jakobovits et al., 1993, Nature 362:255-258; and Bruggermann et al., 1993, Year in Immunol. 7:33. In one example of such a method, transgenic animals are produced by incapacitating the endogenous mouse immunoglobulin loci encoding the mouse heavy and light immunoglobulin chains therein, and inserting into the mouse genome large fragments of human genome DNA containing loci that encode human heavy and light chain proteins. Partially modified animals, which have less than the full complement of human immunoglobulin loci, are then cross-bred to obtain an animal having all of the desired immune system modifications. When administered an immunogen, these transgenic animals produce antibodies that are immunospecific for the immunogen but have human rather than murine amino acid sequences, including the variable regions. For further details of such methods, see, for example, WO96/33735 and WO94/02602. Additional methods relating to transgenic mice for making human antibodies are described in U.S. Pat. Nos. 5,545,807; 6,713,610; 6,673,986; 6,162,963; 5,939,598; 5,545,807; 6,300,129; 6,255,458; 5,877,397; 5,874,299 and 5,545,806; in PCT publications WO91/10741, WO90/04036, WO 94/02602, WO 96/30498, WO 98/24893 and in EP 546073B1 and EP 546073A1.

Human-derived antibodies can also be generated using phage display techniques. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function, if desired. Typically, the Fd fragment (VH-CH1) and light chain (VL-CL) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated. Phage display techniques can also be used in an approach for the humanization of rodent monoclonal antibodies, called "guided selection" (see Jaspers, L. S., et al., Bio/Technology 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

In certain embodiments, the protein comprising an Fc region to be purified according to the methods of the invention is an Fc fusion protein. An "Fc fusion protein" is a protein that contains an Fc region fused or linked to a heterologous polypeptide. Typically, a fusion protein is expressed from a fusion gene in which a nucleotide sequence encoding a polypeptide sequence from one protein (e.g. an Fc region) is appended in frame with, and optionally separated by a linker from, a nucleotide sequence encoding a polypeptide sequence from a different protein. The fusion gene can then be expressed by a recombinant host cell to produce the single fusion protein. The heterologous polypeptide fused to the Fc region may be a polypeptide from a protein other than an immunoglobulin protein. For instance, the heterologous polypeptide may be a ligand polypeptide, a receptor polypeptide, a hormone, cytokine, growth factor, an enzyme, or other polypeptide that is not a component of an immunoglobulin. Such Fc fusion proteins may comprise an Fc region fused to a receptor or fragment thereof or a ligand from a receptor including, but not limited to, any one of the following receptors: both forms of TNFR (referred to as p55 and p75), Interleukin-1 receptors types I and II (as described in EP Patent No. 0460846, U.S. Pat. Nos. 4,968,607, and 5,767,064, which are incorporated by reference herein in their entirety), Interleukin-2 receptor, Interleukin-4 receptor (as described in EP Patent No. 0 367 566 and U.S. Pat. No. 5,856,296, which are incorporated by reference herein in their entirety), Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK, as described in U.S. Pat. No. 6,271,349, which is incorporated by reference herein in its entirety), VEGF receptors, EGF receptor, FGF receptors, receptors for TRAIL (including TRAIL receptors 1, 2, 3, and 4), and receptors that comprise death domains, such as Fas or Apoptosis-Inducing Receptor (AIR). Fc fusion proteins also include peptibodies, such as those described in WO 2000/24782, which is hereby incorporated by reference in its entirety.

In other embodiments, the heterologous polypeptide to which the Fc region is fused or linked may be a polypeptide from an immunoglobulin protein or fragment thereof other than the immunoglobulin from which the Fc region is derived. For example, the heterologous polypeptide may be a heavy chain and/or light chain variable region from a different antibody than the antibody from which the Fc region is obtained. In certain embodiments, the Fc fusion protein comprises at least one single chain Fv fragment (scFv fragment). A "single-chain variable antibody fragment" or "scFv fragment" comprises the VH and VL regions of an antibody, wherein these regions are present in a single polypeptide chain, and optionally comprises a peptide linker between the VH and VL regions that enables the Fv to form the desired structure for antigen binding (see e.g., Bird et al., Science, Vol. 242:423-426, 1988; and Huston et al., Proc. Natl. Acad. Sci. USA, Vol. 85:5879-5883, 1988). In some embodiments, the Fc fusion protein comprises two scFv fragments. In other embodiments, the Fc fusion protein comprises three scFv fragments. In still other embodiments, the Fc fusion protein comprises four scFv fragments.

Figure 5:
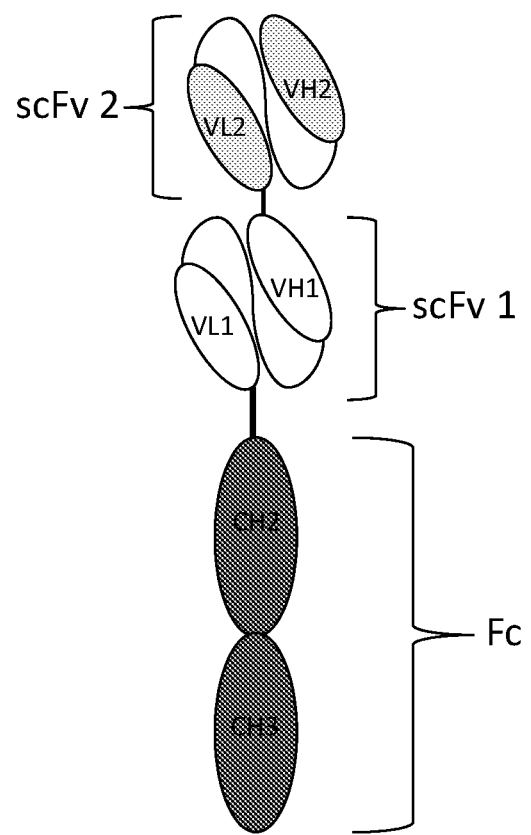
FIG. 5. Structure of single-chain bispecific Fv-Fc binding protein. The figure depicts a schematic representation of a single-chain bispecific Fv-Fc binding protein, an example of an Fc region-containing protein that can be purified by the methods described herein. The single-chain bispecific Fv-Fc binding protein comprises a first scFv fragment, which contains heavy and light chain variable domains from a first antibody, fused to a second scFv fragment, which contains heavy and light chain variable domains from a second antibody, and a Fc region, which is fused at its N-terminus through a peptide linker to the first scFv fragment.

Fc fusion proteins comprising one or more scFv fragments or other fragments of antibody variable regions can have multiple binding sites for one or more antigens. Thus, such Fc fusion proteins can include multispecific, multivalent antigen binding proteins, such as small modular immunopharmaceuticals, described in U.S. Publication No. 20030133939; single chain multivalent binding proteins, described in WO2007/146968, bispecific, bivalent scFv-Fc molecules, described in WO2014144722, and various bispecific antibody molecules, such as IgG-scFv, IgG-Fab, 2scFv-IgG, 4scFv-IgG, VH-IgG, IgG-VH, and Fab-scFv-Fc, and others described in Spiess et al., Mol Immunol., Vol. 67:95-106, 2015 and Kontermann, mAbs, Vol. 4:182-197, 2012. In one embodiment, the Fc fusion protein to be purified according to the methods of the invention is an IgG-scFv binding protein. As used herein, an "IgG-scFv binding protein" is a binding protein comprising two single-chain variable fragments (scFvs), each of which comprises variable domains from a first antibody linked together by a peptide linker, fused to the carboxyl-termini of the heavy chains of a second antibody through another peptide linker. An example of an IgG-scFv binding protein is depicted in FIG. 1. In another embodiment, the Fc fusion protein to be purified according to the methods of the invention is an Fv-Fc binding protein. An "Fv-Fc binding protein" comprises at least one scFv fragment fused, optionally through a linker, to an Fc region. In certain embodiments, the Fv-Fc binding protein comprises two scFv fragments fused to each other, optionally through a linker peptide, which in turn are fused to either the N-terminus or C-terminus of the Fc region. Such bivalent Fv-Fc molecules are described in WO2014144722, which is hereby incorporated by reference in its entirety. One example of such a single-chain bispecific Fv-Fc binding protein is shown in FIG. 5.

Antibodies and Fc fusion proteins that may be purified using the methods described herein may bind to one or more proteins including, but not limited to, CD2, CD3, CD4, CD8, CD11a, CD14, CD18, CD19, CD20, CD22, CD23, CD28, CD25, CD33, CD40, CD44, CD52, CD80 (B7.1), CD86 (B7.2), CD147, IL-1α, IL-1β, IL-4, IL-5, IL-8, IL-10, IL-13, IL-2 receptor, IL-4 receptor, IL-6 receptor, IL-13 receptor, IL-I8 receptor subunits, angiopoietin (e.g. angiopoietin-1, angiopoietin-2, or angiopoietin-4), PDGF-β, VEGF, TGF, TGF-β2, TGF-β1, EGF receptor, VEGF receptor, FGF receptor, C5 complement, Beta-klotho, calcitonin gene-related peptide (CGRP), CGRP receptor, pituitary adenylate cyclase activating polypeptide (PACAP), pituitary adenylate cyclase activating polypeptide type 1 receptor (PAC1 receptor), IgE, tumor antigens, e.g., tumor antigen CA125, tumor antigen MUC1, PEM antigen, PD-1, LCG (which is a gene product that is expressed in association with lung cancer), HER-2, a tumor-associated glycoprotein TAG-72, the SK-1 antigen, integrin alpha 4 beta 7, the integrin VLA-4, B2 integrins, TRAIL receptors 1, 2, 3, and 4, RANK, RANK ligand, sclerostin, Dickkopf-1 (DKK-1), TLA1, TNF-α, the adhesion molecule VAP-1, epithelial cell adhesion molecule (EpCAM), intercellular adhesion molecule-3 (ICAM-3), leukointegrin adhesin, the platelet glycoprotein gp IIb/IIIa, cardiac myosin heavy chain, PCSK9, parathyroid hormone, rNAPc2, MHC I, carcinoembryonic antigen (CEA), alpha-fetoprotein (AFP), tumor necrosis factor (TNF), CTLA-4 (which is a cytotoxic T lymphocyte-associated antigen), Fc-γ-1 receptor, HLA-DR 10 beta, HLA-DR antigen, L-selectin, IPN-γ, respiratory syncytial virus, human immunodeficiency virus (HIV), hepatitis B virus (HBV), *Streptococcus mutans*, and *Staphylococcus aureus*.

Other exemplary Fc region-containing proteins that may be purified according to the methods described herein include, but are not limited to, aflibercept) (Eylea®), alemtuzumab) (Campath®), bevacizumab) (Avastin®), cetuximab) (Erbitux®), panitumumab (Vectibix®), gemtuzumab) (Mylotarg®), evolocumab) (Repatha®), alirocumab) (Praluent®), denosumab (Prolia®), rituximab (Rituxan®), tositumomab (Bexxar®), ibritumomab (Zevalin®), trastuzumab) (Herceptin®), eculizumab) (Soliris®), adalimumab) (Humira®), infliximab) (Remicade®), etanercept) (Enbrel®), daclizumab) (Zenapax®), basiliximab) (Simulect®), palivizumab (Synagis®), omalizumab) (Xolair®), abciximab) (Reopro®), efalizumab) (Raptiva®), pembrolizumab) (Keytruda®), nivolumab) (Opdivo®), natalizumab) (Tysabri®), blinatumomab (Blincyto®), and romiplostim) (Nplate®).

The Fc region-containing protein that is to be purified can be produced by recombinant means, i.e., by living host cells that have been genetically engineered to produce the protein. Methods of genetically engineering cells to produce proteins are well known in the art. See e.g. Ausabel et al., eds. (1990), Current Protocols in Molecular Biology (Wiley, New York). Such methods include introducing nucleic acids that encode and allow expression of the protein into living host cells. These host cells can be prokaryote, yeast, or higher eukaryotic cells, grown in culture. Prokaryotic host cells include eubacteria, such as Gram-negative or Gram-positive organisms, for example, Enterobacteriaceae such as *Escherichia*, e.g., *E. coli, Enterobacter, Erwinia Klebsiella, Proteus, Salmonella*, e.g., *Salmonella typhimurium, Serratia*, e.g., *Serratia marcescans*, and *Shigella*, as well as *Bacillus*, such as *B. subtilis* and *B. licheniformis, Pseudomonas*, and *Streptomyces*. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces*, such as *Schwanniomyces occidentalis*; and filamentous fungi, such as, e.g., *Neurospora, Penicillium, Tolypocladium*, and *Aspergillus* hosts such as *A. nidulans* and *A. niger*. In particular embodiments, the recombinant protein is produced in animal cells, particularly mammalian cells. Mammalian cell lines available as hosts for expression are well known in the art and include, but are not limited to, immortalized cell lines available from the American Type Culture Collection (ATCC), including but not limited to Chinese hamster ovary (CHO) cells, including CHOK1 cells (ATCC CCL61), DXB-11, DG-44, and Chinese hamster ovary cells/-DHFR (CHO, Urlaub et al., Proc. Natl. Acad. Sci. USA 77: 4216, 1980); monkey kidney CV1 line transformed by SV40 (COS-7, ATCC CRL 1651); human embryonic kidney line (293 or 293 cells subcloned for growth in suspension culture, (Graham et al., J. Gen Virol. 36: 59, 1977); baby hamster kidney cells (BHK, ATCC CCL 10); mouse sertoli cells (TM4, Mather, Biol. Reprod. 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68, 1982); MRC 5 cells or FS4 cells; mammalian myeloma cells, and a number of other cell lines. In one particular embodiment, the protein to be purified according to the methods of the invention is recombinantly produced in a mammalian cell line, particularly a CHO cell line.

The methods of the invention can be used to purify or separate the target protein (e.g. an Fc region-containing protein) from one or more impurities in a solution. As used herein, "purifying a protein" refers to a process that reduces the amounts of substances that are different than the target protein and are desirably excluded from the final protein composition. Such impurities or contaminants can include proteins (e.g., soluble or insoluble proteins, or fragments of proteins, including undesired fragments of the protein of interest, such as half antibodies), lipids (e.g., cell wall material), endotoxins, viruses, nucleic acids (e.g., chromosomal or extrachromosomal DNA, t-RNA, rRNA, or mRNA), or combinations thereof, or any other substance that is different from the target Fc region-containing protein of interest. In some embodiments, the impurity or contaminant can originate from the host cell that produced the Fc region-containing protein of interest. For example, in some embodiments, the impurity or contaminant is a host cell protein, host cell nucleic acid (DNA or RNA), or other cellular component of a prokaryotic or eukaryotic host cell that expressed the Fc region-containing protein of interest. In some embodiments, the impurity or contaminant is not derived from the host cell, e.g., the impurity or contaminant could be a protein or other substance from the cell culture media or growth media, a buffer, or a media additive. In other embodiments, impurities or contaminants can be undesired forms of the Fc region-containing protein, such as proteolytic fragments or unassembled components of the protein (e.g. light chains, heavy chains, half molecules or fragments thereof). The term "impurity" as used herein can include a single undesired substance, or a combination of several undesired substances. Suitable methods of detecting contaminating proteins and nucleic acids (e.g. host cell proteins and nucleic acids) are known to those of skill in the art. Such methods include, but are not limited to, enzyme-linked immunosorbent assays (ELISA), gel electrophoresis methods, and quantitative polymerase chain reaction methods. Size exclusion high performance liquid chromatography and capillary electrophoresis methods can be used to measure high molecular weight species (e.g. aggregates) and low molecular weight species (fragments, unassembled components) of the Fc region-containing protein.

A solution from which the target Fc region-containing protein can be purified can be any solution containing the protein and one or more impurities or contaminants, the presence of which is not desired. A solution containing the protein and one or more impurities can include any solution derived from a cell culture in which the target protein has been produced. For example, upon culturing a host cell that has been modified by recombinant means to produce the protein, the Fc region-containing protein can be produced intracellularly, in the periplasmic space, or directly secreted into the medium. If the protein is produced intracellularly, the cells can be lysed according to methods known to those of skill in the art to produce a cell lysate containing the Fc region-containing protein. Thus, in one embodiment, the solution comprising the Fc region-containing protein to be purified is a cell culture lysate. In some embodiments, prior to the purification methods described herein, host cells, lysed fragments, and other large particulates can be removed from the cell culture lysate, for example, by centrifugation, microfiltration, or ultrafiltration. In other embodiments, the recombinant protein is secreted by the host cell into the culture medium. In such embodiments, the recombinant host cells and other particulate matter can be separated from the cell culture medium containing the Fc region-containing protein, for example, by tangential flow filtration or centrifugation to produce a cell culture supernatant. Accordingly, in some embodiments, the solution containing the Fc region-containing protein to be purified is a cell culture supernatant. The cell culture lysate, cell culture supernatant, or other solution containing the Fc region-containing protein may be further clarified to remove fine particulate matter and soluble aggregates prior to the purification methods of the invention. In some embodiments, clarification of solutions can be accomplished by filtering the solutions with a membrane having a pore size between about 0.1 µm and about 0.5 µm, preferably a membrane having a pore size of about 0.22 µm.

In certain embodiments, the solution containing the Fc region-containing protein and one or more impurities is a harvest stream or pool from a bioreactor in which host cells expressing the protein are being cultivated. A "harvest stream" or "harvest pool" refers to a solution which has been processed by one or more operations to separate cells, cell debris, or other large particulates from the Fc region-containing protein. Such operations include standard operations known to those of skill in the art for harvesting recombinant protein from host cell cultures, such as flocculation, centrifugation, and various forms of filtration (e.g. depth filtration, tangential flow microfiltration and tangential flow ultrafiltration). In some embodiments, the solution containing the protein and one or more impurities is a harvest stream or pool from an industrial scale bioreactor (e.g. production bioreactor). Industrial scale bioreactors typically produce volumes of recombinant protein in excess of 500 liters, particularly from 2,000 liters to 20,000 liters. In one particular embodiment, the solution containing one or more impurities and the protein to be purified according to the methods of the invention is a harvest stream or pool from a production bioreactor having a volume of about 2,000 liters or greater.

In certain embodiments, the methods of the invention comprise contacting the solution containing the protein to be purified with a temperature-responsive protein A material. A "temperature-responsive protein A material" refers to a mutant form of protein A, the cell wall protein found in Staphylococcus aureus strains, that has been altered such that its ability to bind to the Fc region of proteins varies with temperature. Such temperature-responsive protein A mutants are described in U.S. Pat. No. 8,198,409, which is hereby incorporated by reference in its entirety. In some embodiments, the temperature-responsive protein A material comprises a mutant protein A that has different Fc region-binding ability at low temperatures, e.g. about 0 to about 15° C., than at higher temperatures, e.g., about 35° C. or higher. In certain embodiments, the temperature-responsive protein A material comprises a mutant protein A comprising an amino sequence of any of the sequences listed in Table 1 below. In one embodiment, the mutant protein A comprises the amino acid sequence of SEQ ID NO: 1. In another embodiment, the mutant protein A comprises the amino acid sequence of SEQ ID NO: 2. In another embodiment, the mutant protein A comprises the amino acid sequence of SEQ ID NO: 4. In still another embodiment, the mutant protein A comprises the amino acid sequence of SEQ ID NO: 6.

TABLE 1

Amino Acid Sequences of Mutant Protein A Proteins

| SEQ ID NO | Amino Acid Sequence |
| --- | --- |
| 1 | ADNKFNKEQQNAFYEILHGPNGNEEQRNAFIQSLKDDPSQSANLLAEAKKLNDAQAPKA |
| 2 | ADNKFNKEQQNAFYEILHAPNGNEEQRNAFIQSLKDDPSQSANLLAEAKKLNDAQAPKA |
| 3 | ADNKFNKEQQNAFYEILHLPNGNEEQRNAFIQSLKDDPSQSANLLAEAKKLNDAQAPKA |
| 4 | ADNKFNKEQQNAFYEILHGPNANEEQRNAFIQSLKDDPSQSANLLAEAKKLNDAQAPKA |
| 5 | ADNKFNKEQQNAFYEILHGPNLEEQRNAFIQSLKDDPSQSANLLAEAKKLNDAQAPKA |
| 6 | ADNKFNKEQQNAFYEILHAPNANEEQRNAFIQSLKDDPSQSANLLAEAKKLNDAQAPKA |
| 7 | ADNKFNKEQQNAFYEILHLPNGNEEQRNAAIQSLKDDPSQSANLLAEAKKLNDAQAPKA |
| 8 | ADNKFNKEQQNAFYEILHLPNGNEEQRNAGIQSLKDDPSQSANLLAEAKKLNDAQAPKA |
| 9 | ADNKFNKEQQNAFYEILHLPNGNEEQRNAFIQSLKDDPSQSANLLAEAKKGNDAQAPKA |
| 10 | ADNKENKEQQNAFYEILHLPNGNEEGRNAFIQSLKDDPSQSANLLAEAKKLNDAQAPKA |
| 11 | ADNKFNKEQQNAFYETLHLPNGNEEQGNAFIQSLKDDPSQSANLLAEAKKLNDAQAPKA |
| 12 | ADNKFNXEQQNAFYEILHGPNANEEQRNAGIQSLKDDPSQSANLLAEAKKLNDAQAPKA |
| 13 | ADNKENKEQQNAFYEILHGPNANEEQRNAFIQSLKDDPSQSANLLAEAKKGNDAQAPKA |
| 14 | ADNKFNKEQQNAFYEILHGPNATEEQRNAFIQSLKDDPSQSANLLAEAKKLNDAQAPKA |

The temperature-responsive protein A material can be made synthetically, for example by peptide synthesis or recombinant technology. Alternatively, the temperature-responsive protein A material can be obtained commercially, for example, from Nomadic Bioscience Co., Ltd. (Byzen Pro® temperature-responsive protein A resin). In some embodiments, the temperature-responsive protein A material is immobilized to a solid phase. Solid phases can include, but are not limited to, beads, resins, gels, particles, membranes, tubes, plates, and films. In one embodiment, the solid phase on which the temperature-responsive protein A is immobilized is a bead, particularly a magnetic bead. In another embodiment, the solid phase on which the temperature-responsive protein A is immobilized is a resin. In certain embodiments in which the temperature-responsive protein A material is immobilized to beads, resins, particles, or other solid phases amenable to packing into a container, the solid phase containing the temperature-responsive protein A material is packed or loaded into a container, such as a column.

Suitable materials from which the solid phase can be manufactured include glass, silica (e.g. silica gel), polysaccharides (e.g., a polysaccharide matrix), such as agarose, dextran, and cellulose, organic polymers, such as polyacrylamide, methylmethacrylate, and polystyrene-divinylbenzene copolymers. Methods of immobilizing the temperature-responsive protein A material to various solid phases are known to those of skill in the art and can include activating materials of the solid phase with functional coupling groups (e.g. carboxyl or thiol groups) and other methods described in U.S. Patent Publication Nos. 2015/0218208 and 2013/0317172.

As used herein, contacting a solution comprising the Fc region-containing protein with the temperature-responsive protein A material or adsorbing the Fc region-containing protein to the temperature-responsive protein A material means the protein is combined with the temperature-responsive protein A material under conditions such that the Fc region-containing protein binds to the material. In particular, the Fc region-containing protein is combined with the temperature-responsive protein A material at a temperature at which the protein binds to the material, for example, at a temperature from about 0° C. to about 15° C., from about 1° C. to about 12° C., or from about 2° C. to about 8° C. In some embodiments, the Fc region-containing protein is contacted with or adsorbed to the temperature-responsive protein A material at a temperature of about 10° C. or less. In certain embodiments, the Fc region-containing protein is contacted with or adsorbed to the temperature-responsive protein A material at a temperature of about 1° C. to about 6° C. In one embodiment, the Fc region-containing protein is contacted with or adsorbed to the temperature-responsive protein A material at a temperature of about 4° C.

In certain embodiments, the temperature-responsive protein A material may be equilibrated with a suitable buffer prior to being contacted with the solution comprising the Fc region-containing protein to be purified. One such suitable equilibration buffer is phosphate buffered saline at pH 7.2. Other suitable equilibration buffers include Tris, BIS, and HEPES at concentrations from about 0.5 mM to about 100 mM comprising physiological salt concentrations (e.g. 150 mM NaCl) at a pH of about 5 to about 9, preferably at a pH of about 6.0 to about 8.0, and more preferably at a pH of about 6.5 to about 7.5.

Once the Fc region-containing protein is bound to the temperature-responsive protein A material, the bound material can be optionally washed with one or more wash solutions prior to elution from the material. The one or more wash solutions are typically buffers at a neutral pH (e.g. about 6.5 to about 7.5) comprising a salt, such as sodium acetate, sodium citrate, or sodium chloride. Suitable concentrations of salt in the wash solutions are from about 0.1 M to about 2 M, about 0.5 M to about 2 M, about 0.75 M to about 1.5 M, or about 0.2 M to about 0.6 M. In certain embodiments, the one or more wash solutions comprise sodium chloride at a concentration of about 0.5 M to about 2 M. In some embodiments, the one or more wash solutions comprise sodium chloride at a concentration of about 0.1 M to about 0.8 M. In one embodiment, the one or more wash solutions comprises about 10 to about 25 mM phosphate buffer and about 0.1 M to about 0.8 M NaCl, at a pH of about 7 to about 7.5. In another embodiment, the one or more wash solutions comprises about 20 to about 50 mM Tris buffer and about 0.1 M to about 0.8 M NaCl, at a pH of about 7 to about 7.5.

The one or more wash buffers may also comprise other components that facilitate the removal of impurities from the temperature-responsive protein A material without significantly affecting the binding interaction of the Fc region-containing protein and the temperature-responsive protein A material. Such additional components can include divalent cations (e.g., calcium, magnesium, and nickel), detergents (e.g., polysorbate 20 or polysorbate 80), or polymers (e.g., polyethylene glycol). In certain embodiments, the temperature of the one or more wash solutions is the same temperature at which the Fc region-containing protein is adsorbed to the temperature-responsive protein A material (e.g. 0° C. to 15° C.). In other embodiments, the temperature of the one or more wash solutions is about 15° C. to 25° C. In still other embodiments, the temperature of the one or more wash solutions does not exceed 25° C., i.e., the temperature of the one or more wash solutions is 25° C. or less, for example between about 1° C. to about 25° C.

Once the Fc region-containing protein is bound to the temperature-responsive protein A material and the bound material is optionally washed as described above, the Fc region-containing protein is removed from the temperature-responsive protein A material using an elution buffer as described herein. Typically, elution of an Fc region-containing protein from a temperature-responsive protein A resin requires that the temperature of the resin be elevated to 35° C. or above. See U.S. Pat. No. 8,198,409 and Koguma et al., Journal of Chromatography A, Vol. 1305: 149-153, 2013. However, the composition of the elution buffer described in detail below allows for proteins bound to the temperature-responsive protein A resin to be removed from the resin at a neutral pH without elevating the temperature of the resin above 35° C. Thus, in certain embodiments, the methods of the invention comprise eluting the bound Fc region-containing protein from the temperature responsive protein A material at a temperature below about 35° C. For example, in some embodiments, the protein is eluted from the temperature-responsive protein A material at a temperature from about 1° C. to about 34° C., from about 4° C. to about 32° C., from about 10° C. to about 30° C., or from about 15° C. to about 25° C. In certain embodiments, the protein is eluted from the temperature-responsive protein A material at a temperature below about 30° C., for example, from about 1° C. to about 25° C. In some embodiments, the protein is eluted from the temperature-responsive protein A material at a temperature from about 20° C. to about 25° C. In other embodiments, the protein is eluted from the temperature-responsive protein A material at a temperature from about 15° C. to about 22° C. In certain embodiments, the protein is eluted from the temperature-responsive protein A material at a temperature below about 10° C., for example, from about 1° C. to about 8° C. In some embodiments, the protein is eluted from the temperature-responsive protein A material at a temperature from about 1° C. to about 6° C. In other embodiments, the protein is eluted from the temperature-responsive protein A material at a temperature from about 2° C. to about 8° C. In some embodiments, the protein is eluted from the temperature-responsive protein A material at the same temperature at which the protein was bound to the material (i.e. the temperature of the material is not altered between the adsorption and elution steps).

In some embodiments, the Fc region-containing protein can be eluted from the temperature-responsive protein A material isocratically with an elution buffer described in detail below. In alternative embodiments, the Fc region-containing protein can be eluted from the temperature-responsive protein A material with a linear gradient, e.g. starting with 100% of solution having a composition similar to a wash solution as described herein and ending with 100% of an elution buffer described in detail below.

The elution buffer employed to remove the Fc region-containing protein from the temperature-responsive protein A material typically is a buffered solution at a pH of about 6.5 to about 7.5. In some embodiments, the pH of the elution buffer is about 6.8 to about 7.5. In other embodiments, the pH of the elution buffer is about 7.2 to about 7.5. In one particular embodiment, the pH of the elution buffer is about 7.0 to about 7.4. Any buffer can be used provided that the buffer is capable of maintaining the pH of the solution in the target pH range (e.g. buffers that have pKa values between 6 and 8). Suitable buffers that buffer in the neutral pH range that can be used as components of the elution buffer in the methods of the invention include, but are not limited to, HEPES (N-[2-hydroxyethyl]piperazine-N'-[2-ethanesulfonic acid]), Tris, phosphate, citrate, MES (2-(N-morpholino) ethanesulfonic acid), BES (N,N-bis[2-hydroxyethyl]-2-aminoethanesulfonic acid), PIPES (piperazine-N,N'-bis(2-ethanesulfonic acid)), Tricine (N-tris[hydroxymethyl] methylglycine), Bicine (N,N-Bis(2-hydroxyethyl)glycine), TES (N-tris[hydroxymethyl]methyl-2-aminoethanesulfonic acid), TAPSO (3-[N-Tris(hydroxymethyl)methylamino]-2-hydroxypropanesulfonic acid), Bis-Tris (Bis(2-hydroxyethyl)amino-tris(hydroxymethyl)methane), and MOPS (3-[N-morpholino]propanesulfonic acid). The buffer can be present in a concentration from about 5 mM to about 200 mM, from about 10 mM to about 150 mM, from about 15 mM to about 100 mM, from about 20 mM to about 75 mM, or from about 25 mM to about 50 mM. In some embodiments, the elution buffer comprises a HEPES buffer, for example in a concentration of about 15 mM to about 100 mM. In other embodiments, the elution buffer comprises a Tris buffer, for example in a concentration of about 15 mM to about 50 mM.

In various embodiments, the elution buffer comprises a chaotropic agent. A "chaotropic agent" is a substance that disrupts the hydrogen bonding network among water molecules and can reduce the order in the structure of macromolecules by affecting intramolecular interactions mediated by non-covalent forces, such as hydrogen bonding, van der Waals forces, and hydrophobic interactions. Without being bound by theory, it is believed that the presence of the chaotropic agent in the elution buffer acts to relax the structure of the Fc region-containing protein to facilitate its disengagement from the temperature-responsive protein A material. Suitable chaotropic agents that can be included in the elution buffer include, but are not limited to, butanol, ethanol, propanol, guanidinium chloride, lithium acetate or lithium perchlorate, magnesium chloride, phenol, sodium dodecyl sulfate, urea, thiourea, and a thiocyanate salt (e.g. sodium thiocyanate, ammonium thiocyanate, or potassium thiocyanate). In certain embodiments, the elution buffer comprises urea, guanidinium chloride, or sodium dodecyl sulfate as the chaotropic agent. In other embodiments, the elution buffer comprises urea, guanidinium chloride, or a thiocyanate salt as the chaotropic agent. In still other embodiments, the elution buffer comprises urea or guanidinium chloride as the chaotropic agent. The chaotropic agent can be present in the elution buffer at a concentration from about 0.4 M to about 5.0 M, from about 0.5 M to about 2.5 M, from about 0.8 M to about 1.2 M, from about 2 M to about 4.5 M, or from about 3 M to about 4.2 M depending on the specific chaotropic agent used. In certain embodiments, the elution buffer comprises urea, for example at a concentration of about 2 M to about 4.5 M. In other embodiments, the elution buffer comprises urea at a concentration of about 3 M to about 4.2 M. In one particular embodiment, the elution buffer comprises urea at a concentration of about 4 M. In some embodiments, the elution buffer comprises guanidinium chloride, for example at a concentration of about 0.5 M to about 2.5 M. In other embodiments, the elution buffer comprises guanidinium chloride at a concentration of about 0.8 M to about 1.2 M. In certain embodiments, the elution buffer comprises guanidinium chloride at a concentration of about 1 M. In other particular embodiments, the elution buffer comprises guanidinium chloride at a concentration of about 2 M.

In certain embodiments, the elution buffer comprises a sugar alcohol in addition to the chaotropic agent. A "sugar alcohol" is an organic compound derived from a sugar and has a structure according to the general formula of $HOCH_2(CHOH)_nCH_2OH$, where n typically varies from 1 to 22 or more. Exemplary sugar alcohols that can be included in the elution buffer include, but are not limited to, glycerol, erythritol, threitol, arabitol, xylitol, ribitol, mannitol, sorbitol, galactitol, fucitol, iditol, volemitol, isomalt, maltitol, lactitol, maltotriitol, and maltotetraitol. In certain embodiments, the elution buffer comprises sorbitol, mannitol, xylitol, or glycerol as the sugar alcohol. In one embodiment, the sugar alcohol in the elution buffer is sorbitol. In another embodiment, the sugar alcohol in the elution buffer is mannitol. The sugar alcohol may be present in the elution buffer at a concentration from about 1 M to about 4.5 M, from about 1.5 M to about 4 M, or from about 2 M to about 2.5 M depending on the specific sugar alcohol selected. In certain embodiments, the elution buffer comprises sorbitol, for example at a concentration of about 1 M to about 4.5 M, more preferably about 2 M to about 2.5 M. In one embodiment, the elution buffer comprises sorbitol at a concentration of about 2.2 M.

Again, without being bound by theory, it is believed that the presence of the sugar alcohol prevents the Fc region-containing protein from completely unfolding in the presence of the chaotropic agent. Thus, in some embodiments, the elution buffer comprises a chaotropic agent and a sugar alcohol in a particular concentration ratio that strikes a balance between relaxing the structure of the Fc region-containing protein so that it disengages from the temperature-responsive protein A material, but preventing the protein from completely unfolding and losing its basic native structure. In such embodiments, the molar concentration ratio of the chaotropic agent to the sugar alcohol is about 0.4 to about 4.5, about 0.8 to about 4, about 1 to about 2, about 1.5 to about 2.5, or about 1.8 to about 2.2. In certain embodiments, the elution buffer comprises urea and sorbitol, wherein the molar concentration ratio of urea to sorbitol is about 1 to about 2.5, or more preferably about 1.1 to about 1.8. In other embodiments, the elution buffer comprises guanidinium chloride and sorbitol, wherein the molar concentration ratio of guanidinium chloride to sorbitol is about 0.5 to about 1.5, or more preferably about 0.5 to about 0.9.

In certain embodiments, the elution buffer may further comprise one or more amino acids. For instance, in some embodiments, the elution buffer may further comprise a basic amino acid, an apolar amino acid, or both a basic amino acid and an apolar amino acid. Without being bound by theory, it is believed that basic amino acids facilitate the dissociation of the Fc region-containing protein from the temperature-responsive protein A material by modulating the charge interactions of the protein with the material, whereas apolar amino acids facilitate the disengagement of the Fc region-containing protein from the temperature-responsive protein A material by modulating the hydrophobic interactions of the protein with the material. As used herein, a "basic amino acid" is a polar amino acid in D or L form that is hydrophilic and positively charged at pH values below its pKa. Exemplary basic amino acids suitable for use in the elution buffer include, but are not limited to, arginine, ornithine, lysine, and histidine. In some embodiments, the elution buffer comprises arginine. In other embodiments, the elution buffer comprises lysine. The basic amino acid can be present in the elution buffer at a concentration from about 0.1 M to about 1.5 M, from about 0.25 M to about 1 M, or from about 0.3 M to about 0.8 M. In certain embodiments, the elution buffer comprises a basic amino acid (e.g. arginine) at a concentration of about 0.5 M.

An "apolar amino acid," used interchangeably herein with "non-polar amino acid," refers to an amino acid in D or L form that contains hydrophobic functional groups and bears no charge at a neutral pH. Exemplary apolar amino acids suitable for use in the elution buffer include, but are not limited to, alanine, cysteine, glycine, isoleucine, leucine, methionine, phenylalanine, proline, tryptophan, and valine. In certain embodiments, the elution buffer comprises proline. The apolar amino acid can be present in the elution buffer at a concentration from about 0.1 M to about 1.5 M, from about 0.25 M to about 1 M, or from about 0.3 M to about 0.8 M. In certain embodiments, the elution buffer comprises an apolar amino acid (e.g. proline) at a concentration of about 0.5 M. In some embodiments, the elution buffer comprises at least one basic amino acid and at least one apolar amino acid. In such embodiments, the basic amino acid and the apolar amino acid can be present in the elution buffer at the same concentration. For example, the basic amino acid and the apolar amino acid can be present in the elution buffer each at a concentration from about 0.25 M to about 1 M, more preferably from about 0.3 M to about 0.8 M. In certain embodiments, the basic amino acid and the apolar amino acid are each present in the elution buffer at a concentration of about 0.5 M. In one embodiment, the elution buffer comprises arginine and proline. In another embodiment, the elution buffer comprises lysine and proline.

In some embodiments, the elution buffer employed in the methods of the invention may further comprise one or more salts. A "salt" refers to an ionic compound resulting from a neutralization reaction of an acid and a base. A salt is typically comprised of an equal number of cations and anions so that the overall net charge of the salt is zero. Suitable salts for inclusion in the elution buffer include, but are not limited to, sodium salts, such as sodium acetate, sodium citrate, sodium chloride, and sodium sulfate; potassium salts, such as potassium acetate, potassium citrate, potassium chloride, and potassium sulfate; and chloride salts, such as sodium chloride, magnesium chloride, nickel chloride, potassium chloride, and ammonium chloride. In certain embodiments, the elution buffer comprises sodium chloride. In other embodiments, the elution buffer comprises potassium chloride. The salt may be included in the elution buffer at a concentration from about 0.1 M to about 1 M, from about 0.25 M to about 0.8 M, from about 0.5 M to about 1 M, or from about 0.5 M to about 0.8 M. In one embodiment, the salt (e.g. sodium chloride) is present in the elution buffer at a concentration of about 0.75 M.

In certain embodiments, the elution buffer used in the methods of the invention has a pH of about 6.5 to about 7.5 and comprises about 5 mM to about 200 mM buffer, about 0.4 M to about 5 M chaotropic agent, about 1 M to about 4.5 M sugar alcohol, about 0.1 M to about 1.5 M apolar amino acid, about 0.1 M to about 1.5 M basic amino acid, and about 0.1 M to about 1 M salt. In some embodiments, the elution buffer has a pH of about 7.0 to about 7.4 and comprises about 15 mM to about 100 mM buffer, about 2 M to about 4.5 M chaotropic agent, about 1 M to about 4.5 M sugar alcohol, about 0.25 M to about 1 M apolar amino acid, about 0.25 M to about 1 M basic amino acid, and about 0.25 M to about 0.8 M salt. In other embodiments, the elution buffer has a pH of about 7.0 to about 7.4 and comprises about 15 mM to about 100 mM buffer, about 0.5 M to about 2.5 M chaotropic agent, about 1 M to about 4.5 M sugar alcohol, about 0.25 M to about 1 M apolar amino acid, about 0.25 M to about 1 M basic amino acid, and about 0.25 M to about 0.8 M salt. In certain embodiments, the elution buffer has a pH of about 7.0 to about 7.4 and comprises about 15 mM to about 100 mM buffer, about 2 M to about 4.5 M chaotropic agent, about 2 M to about 2.5 M sugar alcohol, about 0.25 M to about 1 M apolar amino acid, about 0.25 M to about 1 M basic amino acid, and about 0.25 M to about 0.8 M salt. In some embodiments, the elution buffer has a pH of about 7.0 to about 7.4 and comprises about 15 mM to about 100 mM buffer, about 0.5 M to about 2.5 M chaotropic agent, about 2 M to about 2.5 M sugar alcohol, about 0.25 M to about 1 M apolar amino acid, about 0.25 M to about 1 M basic amino acid, and about 0.25 M to about 0.8 M salt.

For any of the above elution buffer compositions, the buffer can be HEPES or Tris, the chaotropic agent can be urea or guanidinium chloride, the sugar alcohol can be sorbitol or mannitol, the apolar amino acid can be proline, the basic amino acid can be arginine or lysine, and the salt can be a sodium salt, e.g. sodium chloride. For instance, in certain embodiments, the elution buffer has a pH of about 6.5 to about 7.5 and comprises 15 mM to about 100 mM HEPES, about 2 M to about 4.5 M urea, about 1 M to about 4.5 M sorbitol, about 0.25 M to about 1 M proline, about 0.25 M to about 1 M arginine, and about 0.25 M to about 0.8 M sodium chloride. In some embodiments, the elution buffer has a pH of about 7.0 to about 7.4 and comprises about 20 mM to about 75 mM HEPES, about 3 M to about 4.2 M urea, about 2 M to about 2.5 M sorbitol, about 0.3 M to about 0.8 M proline, about 0.3 M to about 0.8 M arginine, and about 0.5 M to about 1 M sodium chloride. In one embodiment, the elution buffer has a pH of about 7.2 and comprises about 25 mM HEPES, about 4 M urea, about 2.2 M sorbitol, about 0.5 M proline, about 0.5 M arginine, and about 0.75 M sodium chloride. In another embodiment, the elution buffer has a pH of about 7.2 and comprises about 50 mM HEPES, about 4 M urea, about 2.2 M sorbitol, about 0.5 M proline, about 0.5 M arginine, and about 0.75 M sodium chloride. In some embodiments, the elution buffer has a pH of about 6.5 to about 7.5 and comprises 15 mM to about 100 mM Tris, about 2 M to about 4.5 M urea, about 1 M to about 4.5 M sorbitol, about 0.25 M to about 1 M proline, about 0.25 M to about 1 M arginine, and about 0.25 M to about 0.8 M sodium chloride. In other embodiments, the elution buffer has a pH of about 6.5 to about 7.5 and comprises 15 mM to about 100 mM HEPES, about 2 M to about 4.5 M urea, about 1 M to about 4.5 M mannitol, about 0.25 M to about 1 M proline, about 0.25 M to about 1 M arginine, and about 0.25 M to about 0.8 M sodium chloride. In still other embodiments, the elution buffer has a pH of about 6.5 to about 7.5 and comprises 15 mM to about 100 mM Tris, about 2 M to about 4.5 M urea, about 1 M to about 4.5 M mannitol, about 0.25 M to about 1 M proline, about 0.25 M to about 1 M arginine, and about 0.25 M to about 0.8 M sodium chloride.

In certain embodiments, the elution buffer has a pH of about 6.5 to about 7.5 and comprises 15 mM to about 100 mM HEPES, about 0.5 M to about 2.5 M guanidinium chloride, about 1 M to about 4.5 M sorbitol, about 0.25 M to about 1 M proline, about 0.25 M to about 1 M arginine, and about 0.25 M to about 0.8 M sodium chloride. In some embodiments, the elution buffer has a pH of about 6.5 to about 7.5 and comprises 15 mM to about 100 mM Tris, about 0.5 M to about 2.5 M guanidinium chloride, about 1 M to about 4.5 M sorbitol, about 0.25 M to about 1 M proline, about 0.25 M to about 1 M arginine, and about 0.25 M to about 0.8 M sodium chloride. In other embodiments, the elution buffer has a pH of about 6.5 to about 7.5 and comprises 15 mM to about 100 mM HEPES, about 0.5 M to about 2.5 M guanidinium chloride, about 1 M to about 4.5 M mannitol, about 0.25 M to about 1 M proline, about 0.25 M to about 1 M arginine, and about 0.25 M to about 0.8 M sodium chloride. In still other embodiments, the elution buffer has a pH of about 6.5 to about 7.5 and comprises 15 mM to about 100 mM Tris, about 0.5 M to about 2.5 M guanidinium chloride, about 1 M to about 4.5 M mannitol, about 0.25 M to about 1 M proline, about 0.25 M to about 1 M arginine, and about 0.25 M to about 0.8 M sodium chloride.

In some embodiments, the methods of the invention reduce or eliminate aggregation of the Fc region-containing protein than can occur during purification procedures. Accordingly, the present invention also includes a method for reducing aggregation during purification of a protein comprising an Fc region. In one embodiment, the method comprises adsorbing the Fc region-containing protein to a temperature-responsive protein A material at a temperature at which the protein binds to the material; and eluting the protein from the material at a temperature below about 35° C. with an elution buffer having a pH of about 6.5 to about 7.5 and comprising a chaotropic agent, a sugar alcohol, an apolar amino acid, and a basic amino acid, wherein the amount of the Fc region-containing protein in aggregated form in the eluate is less than the amount in an eluate from a conventional protein A material.

As used herein, an "aggregated form" of an Fc region-containing protein refers to a multimeric form of the protein comprised of multiple molecules or monomers of the protein held together by non-covalent interactions. A "monomeric form" of an Fc region-containing protein refers to the form of the protein comprising a single complete molecule of the protein, including all components and chains. For instance, an antibody monomer or monomeric form of an antibody consists of two light chains and two heavy chains connected by disulfide bonds. Similarly, a monomeric form of an IgG-scFv binding protein comprises two light chains and two modified heavy chains connected by disulfide bonds, wherein each modified heavy chain comprises a single-chain variable fragment fused to its carboxyl-terminus. The monomeric form of an IgG-scFv binding protein is shown in FIG. 1. For single-chain Fc region-containing proteins, such as the single-chain bispecific Fv-Fc binding depicted in FIG. 5, the monomeric form is the single polypeptide chain.

In some embodiments of the purification methods described herein, a substantial proportion of the Fc region-containing protein in the eluate from the temperature-responsive protein A material is in monomeric form. For example, at least 60%, at least 65%, at least 70%, at least 75%, at least 80%, at least 85%, at least 90%, at least 95%, at least 96%, at least 97%, at least 98%, or at least 99% of the Fc region-containing protein in the eluate from the temperature-responsive protein A material resulting from the elution with an elution buffer described herein is in monomeric form. In certain embodiments, at least 70% of the Fc region-containing protein in the eluate from the material is in monomeric form. In some embodiments, at least 80% of the Fc region-containing protein in the eluate from the material is in monomeric form. In other embodiments, at least 90% of the Fc region-containing protein in the eluate from the material is in monomeric form.

In certain embodiments of the purification methods described herein, the amount of the Fc region-containing protein in aggregated form in the eluate from the temperature-responsive protein A material using an elution buffer described herein is less than the amount of the Fc region-containing protein in aggregated form in an eluate from a conventional protein A material. As used herein, "conventional protein A material" refers to a native or wild-type form of Protein A found in *Staphylococcus aureus* strains that loses its affinity for Fc regions of protein under acidic conditions (e.g. at pH lower than about 6). Conventional protein A material includes commercially available protein A resins, such as Mab Select SuRe™ resin (GE Healthcare), CaptivA® resin (Repligen), protein A resins from Thermo Fisher, GenScript, and Bio-Rad, and the like. Typical conditions for eluting a protein from conventional protein A material include the use of an acidic elution buffer, such as an acetic acid buffer at a pH of about 2.5 to about 4. In some embodiments, the amount of the Fc region-containing protein in aggregated form in the eluate from the temperature-responsive protein A material using an elution buffer described herein is less than the amount of the Fc region-containing protein in aggregated form in an eluate from a conventional protein A material using an acetic acid buffer (e.g. 1% acetic acid) having a pH of about 2.5 to about 4.

The amount of the Fc region-containing protein in aggregated form in the eluate from the temperature-responsive protein A material using an elution buffer described herein is preferably less than 50%, less than 45%, less than 40%, less than 35%, less than 30%, less than 25%, less than 20%, less than 15%, less than 10%, less than 5%, less than 4%, less than 3%, less than 2%, or less than 1%. In certain embodiments, less than 30% of the Fc region-containing protein in the eluate from the temperature-responsive protein A material is in aggregated form. In some embodiments, less than 20% of the Fc region-containing protein in the eluate from the temperature-responsive protein A material is in aggregated form. In other embodiments, less than 10% of the Fc region-containing protein in the eluate from the temperature-responsive protein A material is in aggregated form.

Methods of detecting and quantitating aggregated and monomeric forms of proteins are known to those of skill in the art and can include size-exclusion high performance liquid chromatographic methods, such as those described in the examples. Other suitable methods include sedimentation velocity analytical ultracentrifugation, asymmetrical flow field flow fractionation, and dynamic light scattering. See, e.g., Gabrielson et al., Journal of Pharmaceutical Sciences, Vol. 96: 268-279, 2007.

In certain embodiments of the methods of the invention, following elution from the temperature-responsive protein A material, the Fc region-containing protein can be subject to further purification steps. For example, in some embodiments, the Fc region-containing protein eluted from the temperature-responsive protein A material is subject to one or more additional chromatography steps. Such additional chromatography steps can include ion exchange chromatography (e.g. cation exchange chromatography or anion exchange chromatography), hydrophobic interaction chromatography, mixed mode chromatography, size-exclusion chromatography (e.g. gel filtration chromatography), hydroxyapatite chromatography, metal affinity chromatography, or combinations thereof. The additional chromatography steps can be performed in bind and elute mode, in which the target protein binds to the chromatographic material and impurities flow through, or flow through mode, in which the impurities bind to the chromatographic material and the target protein flows through. In some embodiments, the Fc region-containing protein eluted from the temperature-responsive protein A material is subject to cation exchange chromatography. In other embodiments, the Fc region-containing protein eluted from the temperature-responsive protein A material is subject to anion exchange chromatography. In certain embodiments, the Fc region-containing protein eluted from the temperature-responsive protein A material is subject to hydrophobic interaction chromatography. In still other embodiments, the Fc region-containing protein eluted from the temperature-responsive protein A material is subject to mixed mode chromatography. In certain other embodiments, the Fc region-containing protein eluted from the temperature-responsive protein A material is subject to size exclusion chromatography (e.g. gel filtration chromatography), such as the size exclusion chromatography method described in further detail below.

The chromatography steps of the methods of the invention can be followed by additional steps, such as viral inactivation, viral filtration and/or ultrafiltration/diafiltration steps. For instance, in some embodiments, a viral inactivation step using detergent or UV inactivation methods may be conducted with the eluate pool or effluent from the temperature-responsive protein A material. In one embodiment, the Fc region-containing protein eluted from the temperature-responsive protein A material is subject to a detergent viral inactivation step. A detergent, such as Triton X-100 (e.g. at a concentration of 1% v/v), can be added to the eluate pool or effluent from the temperature-responsive protein A material and incubated at neutral pH for about 30 min to about 60 min to inactivate any viruses present.

The present invention also provides a method for separating an antibody from a half antibody form thereof. As described in Example 5, it was surprisingly found that the elution buffers described herein for eluting Fc region-containing proteins from a temperature-responsive protein A resin at neutral pH and constant temperature could be used as a mobile phase in size exclusion chromatography to efficiently separate antibodies from half antibody forms thereof. Accordingly, in certain embodiments, the present invention includes a method for separating antibodies from half antibody forms thereof, the method comprising contacting a solution comprising antibodies and half antibody forms thereof with a gel filtration matrix using a mobile phase having a pH of about 6.5 to about 7.5 and comprising a chaotropic agent, a sugar alcohol, an apolar amino acid, and a basic amino acid; and collecting elution fractions from the gel filtration matrix, wherein the antibodies are eluted in one set of elution fractions and the half antibody forms thereof are eluted in another set of elution fractions, thereby separating the antibodies from the half antibody forms thereof.

Figure 9A:
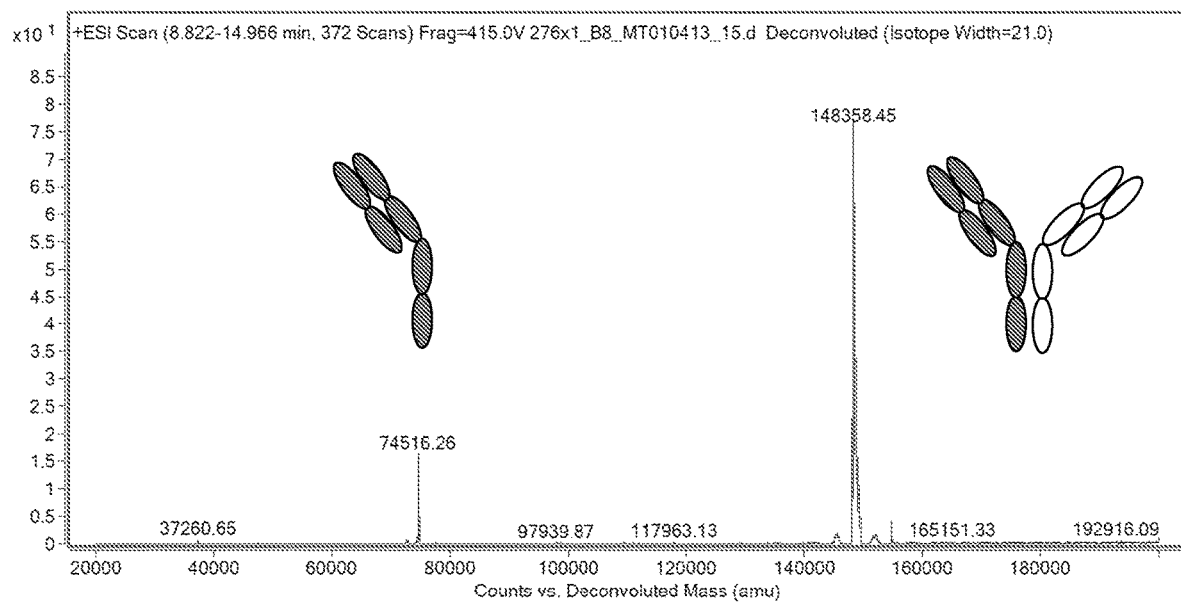
FIGS. 9A and 9B. The figures depict LCMS chromatograms from two different lots of a recombinant bispecific heterodimeric antibody following conventional protein A purification. The fully assembled heterodimeric antibody, which has a predicted mass of 148351 daltons, and one species of half antibody, which has a predicted mass of 74355 daltons, are detected in both lots. The other species of half antibody, which has a predicted mass of 74004 daltons, is not detected. The levels of the half antibody vary from lot to lot.
Figure 9B:
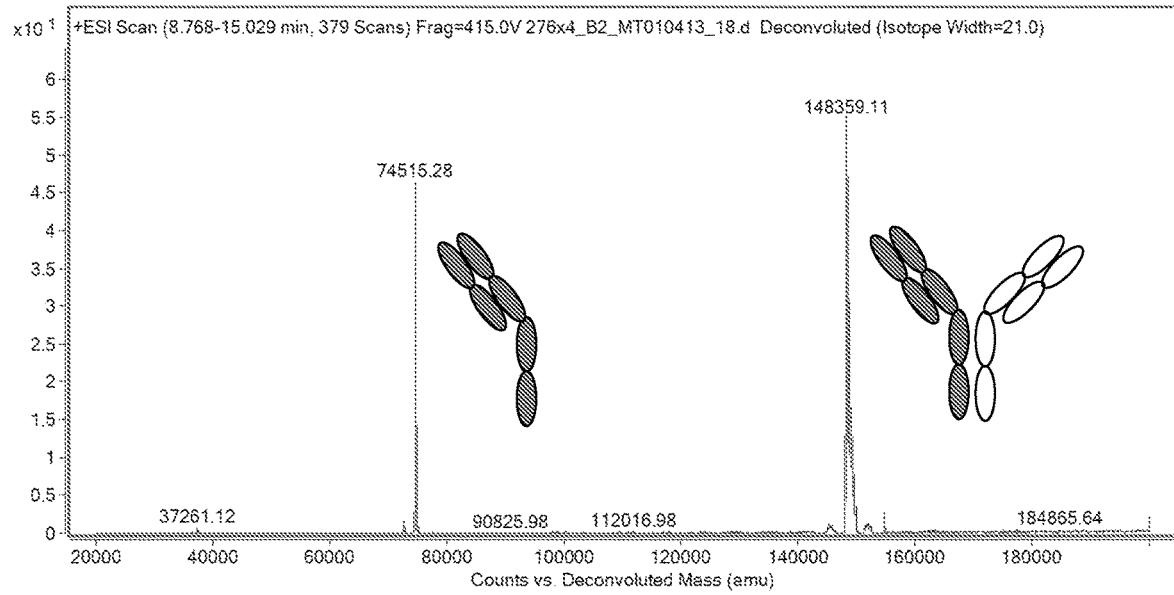

"Half antibodies" refer to a form of the antibodies of interest that typically comprise a single light chain polypeptide and a single heavy chain polypeptide (see schematic on the left side of FIGS. 9A and 9B). Half antibodies (used interchangeably with "half molecules") generally result from incompletion of the assembly or disruption of the interaction between the two heavy chain polypeptides of an antibody (e.g. disruption of inter-polypeptide disulfide bond formation between the hinge regions of the two heavy chains). In certain embodiments, the antibodies to be separated from their half antibody forms are multi-specific (e.g. bispecific) heterodimeric antibodies. In such embodiments, two species of half antibodies can result from recombinant production of bispecific heterodimeric antibodies: one half antibody that binds to the first antigen and another half antibody that binds to a second antigen. The methods of the invention can separate one or both species of half antibodies from the fully assembled antibodies.

In some embodiments of the methods of separating an antibody from a half antibody form thereof, the methods comprise contacting a solution containing the antibody to be purified and half antibody forms thereof with a gel filtration matrix. The gel filtration matrix is typically comprised of porous beads made of cross-linked polymers that can be packed in a column or other container. Various types of gel filtration matrices suitable for use in the methods of the invention are commercially available and include, but are not limited to, dextran-based gels, such as SEPHADEX (cross-linked dextran and epichlorohydrin); polyacrylamide-based gels, such as SEPHACRYL (cross-linked copolymer of allyl dextran and N,N'-methylenebisacrylamide); agarose-based gels, such as SUPEROSE (highly cross-linked agarose) or SEPHAROSE (cross-linked agarose); and composite gels prepared from two kinds of gels, such as SUPERDEX (cross-linked dextran and agarose). In certain embodiments, the gel filtration matrix comprises cross-linked agarose and dextran. For example, in one embodiment, the gel filtration matrix is a SUPERDEX gel filtration matrix (GE Healthcare), such as the SUPERDEX 200 gel filtration matrix. The fractionation range of the gel filtration matrix may be from about 5 kDa to about 5000 kDa, about 10 kDa to about 1500 kDa, or about 10 kDa to about 600 kDa. In some embodiments, the fractionation range of the gel filtration matrix employed in the methods of the invention is from about 10 kDa to about 600 kDa.

The mobile phase for the size exclusion chromatography to separate the fully assembled antibodies from half antibodies can be any of the elution buffers described herein for eluting Fc region-containing proteins from a temperature-responsive protein A resin at neutral pH and constant temperature. In certain embodiments, the mobile phase has a pH of about 6.5 to about 7.5 and comprises a chaotropic agent, a sugar alcohol, an apolar amino acid, and a basic amino acid. The mobile phase will generally be a buffered solution at a pH of about 6.5 to about 7.5. In some embodiments, the pH of the mobile phase is about 6.8 to about 7.5. In other embodiments, the pH of the mobile phase is about 7.2 to about 7.5. In one particular embodiment, the pH of the mobile phase is about 7.0 to about 7.4. Suitable buffers and concentrations that buffer in this pH range are described in detail above. In some embodiments, the mobile phase comprises a HEPES buffer, for example in a concentration of about 15 mM to about 100 mM. In other embodiments, the mobile phase comprises a Tris buffer, for example in a concentration of about 15 mM to about 50 mM.

The chaotropic agent used in the mobile phase can be any of the chaotropic agents at any of the concentrations described above. For instance, the chaotropic agent in the mobile phase can be urea, guanidinium chloride, sodium thiocyanate, potassium thiocyanate, or ammonium thiocyanate. In one particular embodiment, the mobile phase comprises urea as the chaotropic agent. In such embodiments, urea is present in the mobile phase at a concentration of about 2 M to about 4.5 M. In some embodiments, the mobile phase comprises urea at a concentration of about 3 M to about 4.2 M. In other embodiments, urea is present in the mobile phase at a concentration of about 4 M.

The mobile phase also preferably comprises a sugar alcohol, which can be any of those described above for inclusion in elution buffers. In some embodiments, the mobile phase comprises sorbitol, mannitol, xylitol, or glycerol as the sugar alcohol. In one embodiment, the sugar alcohol in the mobile phase is sorbitol. In another embodiment, the sugar alcohol in the mobile phase is mannitol. The sugar alcohol may be present in the mobile phase at a concentration from about 1 M to about 4.5 M, from about 1.5 M to about 4 M, or from about 2 M to about 2.5 M depending on the specific sugar alcohol selected. In certain embodiments, the mobile phase comprises sorbitol, for example at a concentration of about 1 M to about 4.5 M, more preferably about 2 M to about 2.5 M. In one embodiment, the mobile phase comprises sorbitol at a concentration of about 2.2 M.

In certain embodiments, the mobile phase may further comprise one or more amino acids, such as those described above for inclusion in elution buffers of the invention. For instance, in some embodiments, the mobile phase may further comprise a basic amino acid, an apolar amino acid, or both a basic amino acid and an apolar amino acid. In certain embodiments, the mobile phase comprises a basic amino acid selected from histidine, lysine, ornithine, and arginine. In some embodiments, the mobile phase comprises arginine. In other embodiments, the mobile phase comprises lysine. The basic amino acid can be present in the mobile phase at a concentration from about 0.1 M to about 1.5 M, from about 0.25 M to about 1 M, or from about 0.3 M to about 0.8 M. In certain embodiments, the mobile phase comprises a basic amino acid (e.g. arginine) at a concentration of about 0.5 M.

In some embodiments, the mobile phase comprises an apolar amino acid selected from alanine, cysteine, glycine, isoleucine, leucine, methionine, phenylalanine, proline, tryptophan, and valine. In particular embodiments, the mobile phase comprises proline. The apolar amino acid can be present in the mobile phase at a concentration from about 0.1 M to about 1.5 M, from about 0.25 M to about 1 M, or from about 0.3 M to about 0.8 M. In certain embodiments, the mobile phase comprises an apolar amino acid (e.g. proline) at a concentration of about 0.5 M. In some embodiments, the mobile phase comprises at least one basic amino acid and at least one apolar amino acid. In such embodiments, the basic amino acid and the apolar amino acid can be present in the mobile phase at the same concentration. For example, the basic amino acid and the apolar amino acid can be present in the mobile phase each at a concentration from about 0.25 M to about 1 M, more preferably from about 0.3 M to about 0.8 M. In certain embodiments, the basic amino acid and the apolar amino acid are each present in the mobile phase at a concentration of about 0.5 M. In one embodiment, the mobile phase comprises arginine and proline. In another embodiment, the mobile phase comprises lysine and proline.

In some embodiments, the mobile phase employed in the size exclusion chromatography-based methods to separate full antibodies from half antibodies may further comprise one or more salts, such as any of those described above for inclusion in the elution buffers of the invention. In certain embodiments, the mobile phase comprises sodium chloride. In other embodiments, the mobile phase comprises potassium chloride. The salt may be included in the mobile phase at a concentration from about 0.1 M to about 1 M, from about 0.25 M to about 0.8 M, from about 0.5 M to about 1 M, or from about 0.5 M to about 0.8M. In one embodiment, the salt (e.g. sodium chloride) is present in the mobile phase at a concentration of about 0.75 M.

In certain embodiments, the mobile phase used in the methods of the invention has a pH of about 6.5 to about 7.5 and comprises about 5 mM to about 200 mM buffer, about 0.4 M to about 5 M chaotropic agent, about 1 M to about 4.5 M sugar alcohol, about 0.1 M to about 1.5 M apolar amino acid, about 0.1 M to about 1.5 M basic amino acid, and about 0.1 M to about 1 M salt. In some embodiments, the mobile phase has a pH of about 7.0 to about 7.4 and comprises about 15 mM to about 100 mM buffer, about 2 M to about 4.5 M chaotropic agent, about 1 M to about 4.5 M sugar alcohol, about 0.25 M to about 1 M apolar amino acid, about 0.25 M to about 1 M basic amino acid, and about 0.25 M to about 0.8 M salt. In other embodiments, the mobile phase has a pH of about 7.0 to about 7.4 and comprises about 15 mM to about 100 mM buffer, about 2 M to about 4.5 M chaotropic agent, about 2 M to about 2.5 M sugar alcohol, about 0.25 M to about 1 M apolar amino acid, about 0.25 M to about 1 M basic amino acid, and about 0.25 M to about 0.8 M salt. For any of the above-described mobile phase compositions, the buffer can be HEPES or Tris, the chaotropic agent can be urea or guanidinium chloride, the sugar alcohol can be sorbitol or mannitol, the apolar amino acid can be proline, the basic amino acid can be arginine or lysine, and the salt can be a sodium salt, e.g. sodium chloride. For example, in certain embodiments, the mobile phase has a pH of about 6.5 to about 7.5 and comprises 15 mM to about 100 mM HEPES, about 2 M to about 4.5 M urea, about 1 M to about 4.5 M sorbitol, about 0.25 M to about 1 M proline, about 0.25 M to about 1 M arginine, and about 0.25 M to about 0.8 M sodium chloride. In some embodiments, the mobile phase has a pH of about 7.0 to about 7.4 and comprises about 20 mM to about 75 mM HEPES, about 3 M to about 4.2 M urea, about 2 M to about 2.5 M sorbitol, about 0.3 M to about 0.8 M proline, about 0.3 M to about 0.8 M arginine, and about 0.5 M to about 1 M sodium chloride. In one embodiment, the mobile phase has a pH of about 7.2 and comprises about 25 mM HEPES, about 4 M urea, about 2.2 M sorbitol, about 0.5 M proline, about 0.5 M arginine, and about 0.75 M sodium chloride. In another embodiment, the mobile phase has a pH of about 7.2 and comprises about 50 mM HEPES, about 4 M urea, about 2.2 M sorbitol, about 0.5 M proline, about 0.5 M arginine, and about 0.75 M sodium chloride.

In some embodiments, the mobile phase has a pH of about 6.5 to about 7.5 and comprises 15 mM to about 100 mM Tris, about 2 M to about 4.5 M urea, about 1 M to about 4.5 M sorbitol, about 0.25 M to about 1 M proline, about 0.25 M to about 1 M arginine, and about 0.25 M to about 0.8 M sodium chloride. In other embodiments, the mobile phase has a pH of about 6.5 to about 7.5 and comprises 15 mM to about 100 mM HEPES, about 2 M to about 4.5 M urea, about 1 M to about 4.5 M mannitol, about 0.25 M to about 1 M proline, about 0.25 M to about 1 M arginine, and about 0.25 M to about 0.8 M sodium chloride. In still other embodiments, the mobile phase has a pH of about 6.5 to about 7.5 and comprises 15 mM to about 100 mM Tris, about 2 M to about 4.5 M urea, about 1 M to about 4.5 M mannitol, about 0.25 M to about 1 M proline, about 0.25 M to about 1 M arginine, and about 0.25 M to about 0.8 M sodium chloride.

The flow rate of the mobile phase through the gel filtration matrix can be adjusted to further enhance the separation between the antibodies and the half antibody forms thereof. As described in Example 5, increasing the flow rate of the mobile phase resulted in a loss in efficiency of separation between the fully assembled antibodies and the half antibodies. Thus, in certain embodiments, slower flow rates are preferred. In some embodiments, the flow rate of the mobile phase is applied to the gel filtration matrix at a flow rate of about 0.01 ml/min to about 0.2 ml/min. In other embodiments, the flow rate of the mobile phase is applied to the gel filtration matrix at a flow rate of about 0.02 ml/min to about 0.06 ml/min.

Figure 12:
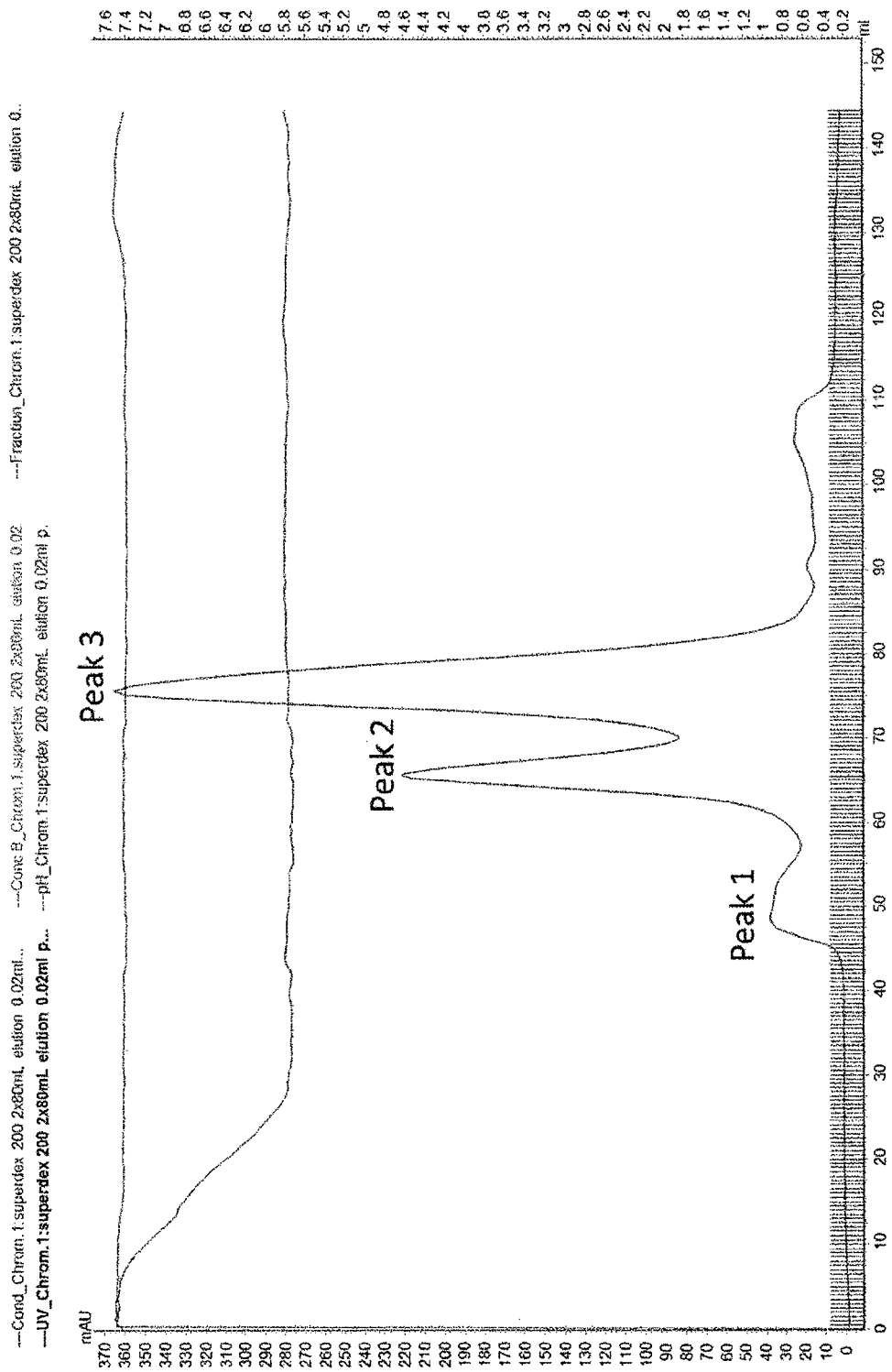
FIG. 12. Elution profile from a preparative SEC gel filtration column (2×80 ml Superdex 200) of a conventional protein A eluate pool of a bispecific heterodimeric antibody ("heterodimeric antibody A"). The SEC was conducted with a mobile phase comprising 50 mM HEPES, 0.75 M NaCl, 0.5 M arginine, 0.5 M proline, 2.2 M sorbitol, and 4 M urea at pH 7.2 at a flow rate of 0.02 ml/min. Three primary protein peaks are observed.

As the solution comprising antibodies and half antibody forms thereof is moved through the gel filtration matrix with the mobile phase described herein, elution fractions are collected. The protein content of the fractions can be monitored using UV absorption, e.g. at 280 nm, and the elution fractions comprising the fully assembled antibodies can be collected, whereas the fractions containing higher molecular weight aggregates and the half antibodies can be discarded. As shown in FIG. 12, when the size exclusion chromatography is operated according to the methods of the invention, aggregates of the antibody and other higher molecular weight contaminants elute from the gel filtration matrix first, followed by the fully assembled antibodies, and then the half antibodies. Samples from the elution fractions can be analyzed by SDS-PAGE and/or analytical SE-HPLC as described in Example 5 to verify the enrichment of the fractions for the fully assembled antibodies and removal of half antibodies.

The size exclusion chromatography-based method (e.g. gel filtration chromatography-based method) to separate antibodies from half antibodies can be conducted after one or more purification procedures or other unit operations. For example, the size exclusion chromatography-based method can be a second or third polish chromatography in a purification process for antibodies, particularly multi-specific heterodimeric antibodies. In some embodiments, the size exclusion chromatography-based method is performed following a protein A affinity chromatography purification step. Thus, the solution containing antibodies and half antibody forms thereof is an eluate pool or effluent stream from a protein A chromatography. The protein A chromatography can be a conventional protein A chromatography. Alternatively, the protein A chromatography can be the protein A chromatography method described herein. Because the elution buffer employed in the methods of the invention to remove Fc region-containing proteins, such as antibodies, from a temperature-responsive protein A material has the same composition as the mobile phase used in the gel filtration chromatography-based methods, these two purification procedures can be used sequentially. Thus, in certain embodiments, the present invention provides a method for purifying an antibody comprising: (i) contacting a solution comprising the antibody and one or more impurities (e.g. half antibody forms thereof) with a temperature-responsive protein A material at a temperature at which the antibody binds to the material; (ii) eluting the antibody from the material at a temperature below about 35° C. with an elution buffer having a pH of about 6.5 to about 7.5 and comprising a chaotropic agent, a sugar alcohol, an apolar amino acid, and a basic amino acid; (iii) contacting the eluate from the temperature-responsive protein A material with a gel filtration matrix using the elution buffer as the mobile phase; and (iv) collecting elution fractions from the gel filtration matrix comprising the antibody. In certain embodiments, the antibody to be purified is a multi-specific heterodimeric antibody. The temperature-responsive protein A chromatography step and the gel filtration chromatography step can be operated in a continuous manner, such that the eluate stream from the temperature-responsive protein A chromatography is directly loaded onto a gel filtration matrix without any intervening hold tanks. In some embodiments, a detergent or UV viral inactivation step can be optionally incorporated between the temperature-responsive protein A chromatography step and the gel filtration chromatography step.

The following examples, including the experiments conducted and the results achieved, are provided for illustrative purposes only and are not to be construed as limiting the scope of the appended claims.

EXAMPLES

Example 1

Purification of an IgG-scFv Binding Protein

This example describes the purification of one type of Fc region-containing protein, an IgG-scFv binding protein, using either conventional protein A chromatography or the affinity chromatography method of the invention. An IgG-scFv binding protein comprises two single-chain variable fragments (scFvs), each containing heavy and light chain variable domains from a first antibody, fused through peptide linkers to the carboxyl-termini of the heavy chains of a second antibody. The resulting molecule is a tetravalent binding protein having two antigen binding domains against a first target located on the amino terminal side of an immunoglobulin Fc region and two antigen binding domains against a second target located on the carboxyl terminal side of the Fc region. The monomeric form of the IgG-scFv is shown in FIG. 1.

Figure 2:
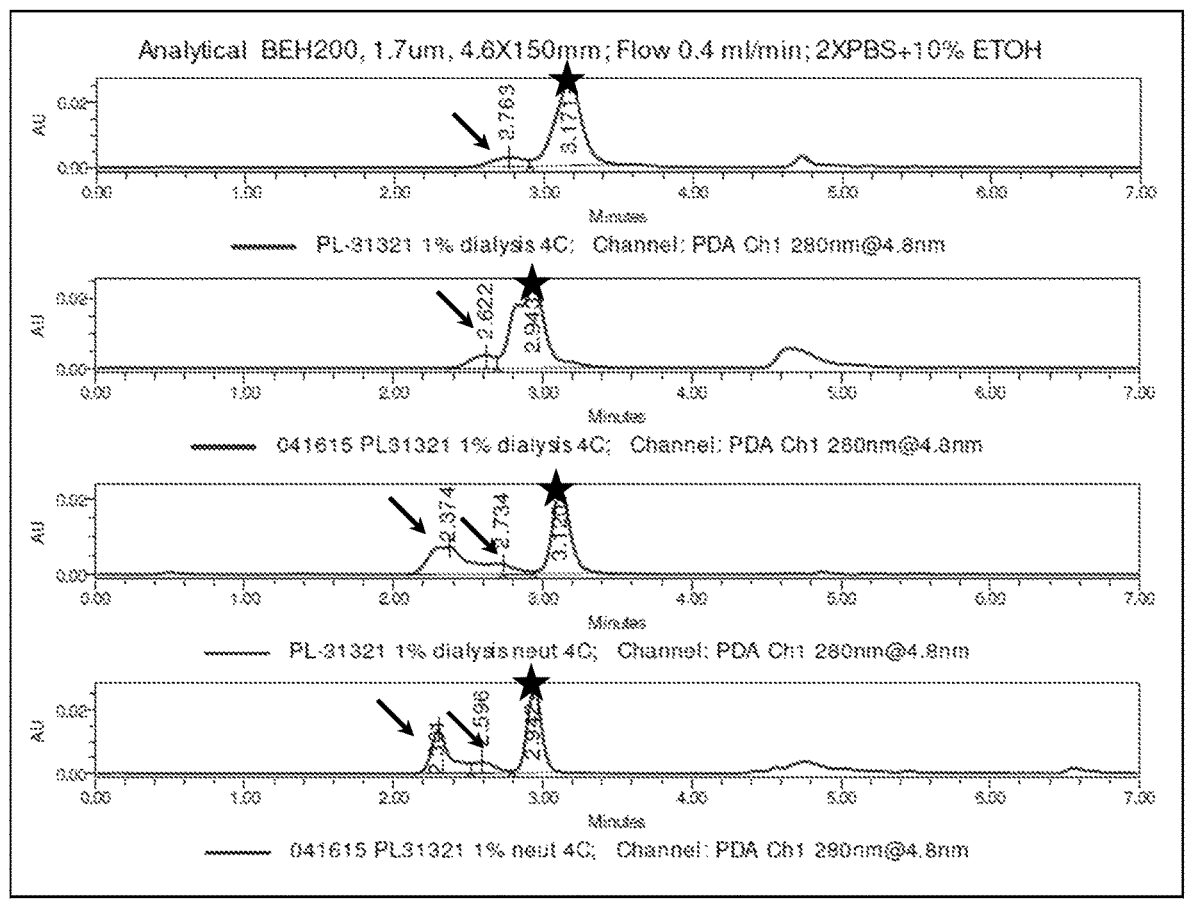
FIG. 2. IgG-scFv binding protein eluted from conventional protein A column. The figure shows SE-UPLC chromatograms from samples of the protein A eluate pools of an IgG-scFv binding protein. The binding proteins were eluted from a conventional protein A chromatography column using a 1% acetic acid buffer, pH 2.7 at 4° C. The eluates off the SEC-UPLC column contained both aggregate peaks (denoted by black arrows) and a monomer peak (denoted by a black star). Each of the four panels is a separate experiment.

For comparative purposes, the IgG-scFv binding protein was purified using conventional protein A affinity chromatography. Between 100-250 ml of cell culture medium containing cells expressing the IgG-scFv binding protein was subjected to low speed centrifugation (600 rpm) at 4° C. for 15 minutes in order to sediment the cells and cell debris. The resulting clarified supernatant solution was passed through a 0.22 micron filter to remove fine particulates and soluble aggregates. The clarified and filtered solution was loaded on to a column containing MabSelect SuRe™ resin (GE Healthcare) at a flow rate of 1 ml/min and at a temperature of 4° C. After washing the column with a phosphate buffered saline solution containing 0.5 M NaCl at pH 7.2, the bound IgG-scFv binding protein was eluted from the conventional protein A resin using a 174 mM (1%) acetic acid solution at pH 2.7 and at a temperature of 4° C. A sample of the eluate pool was analyzed by size exclusion—ultrahigh performance liquid chromatography (SE-UPLC) using a Superdex 200 analytical gel filtration column. The results of four independent experiments are shown in FIG. 2. In one experiment, the protein was eluted with the low pH acetic acid buffer without neutralization to pH 7.2 (top panel in FIG. 2). In a second experiment, the protein was eluted with the low pH acetic acid buffer and neutralized immediately to pH 7.2 (second panel in FIG. 2). In a third experiment, the protein was eluted with the low pH acetic acid buffer and stored for eight weeks in the low pH acetic acid buffer without neutralization (third panel in FIG. 2). In a fourth experiment, the protein was eluted with the low pH acetic acid buffer and stored for eight weeks in the low pH acetic acid buffer before neutralization to pH 7.2 (bottom panel in FIG. 2).

As shown by the SE-UPLC profiles, the IgG-scFv binding proteins have a high tendency to aggregate during the low pH elution from the conventional protein A affinity column as evidenced by the multiple peaks (denoted by black arrows) eluting before the monomer peak (denoted by a black star) in the chromatograms. Both the acid exposure and pH jump from the low pH to neutral pH induce aggregation of the IgG-scFv binding protein with the pH jump having a greater adverse effect than the acid exposure alone. Loading and elution of the conventional protein A column were also conducted at room temperature and results similar to those shown in FIG. 2 were obtained (data not shown).

In a second series of experiments, the IgG-scFv binding protein was purified using a temperature-responsive protein A resin and a particular elution buffer that allowed the elution of the binding protein from the temperature-responsive protein A resin without elevating the temperature of the column above room temperature. To prepare the temperature-responsive protein A (TR-ProA) column, approximately 25 mls of suspended TR-ProA resin (Byzen Pro®, Nomadic Bioscience Co., LTD.) were packed in a 15 ml column to a final volume of fifteen milliliters. The column was washed with five column volumes of Solution A (phosphate buffered saline (PBS), pH 7.2). The column was then washed with Solution B (PBS containing 0.5 M NaCl) followed by rinsing with ten column volumes of water. The rinsed column was then washed with fifteen column volumes of elution buffer, which contained 25 or 50 mM HEPES, 0.75 M NaCl, 0.5 M arginine, 0.5 M proline, 2.2 M sorbitol, and 4 M urea at pH 7.2. The column was then equilibrated with Solution A.

Figure 3:
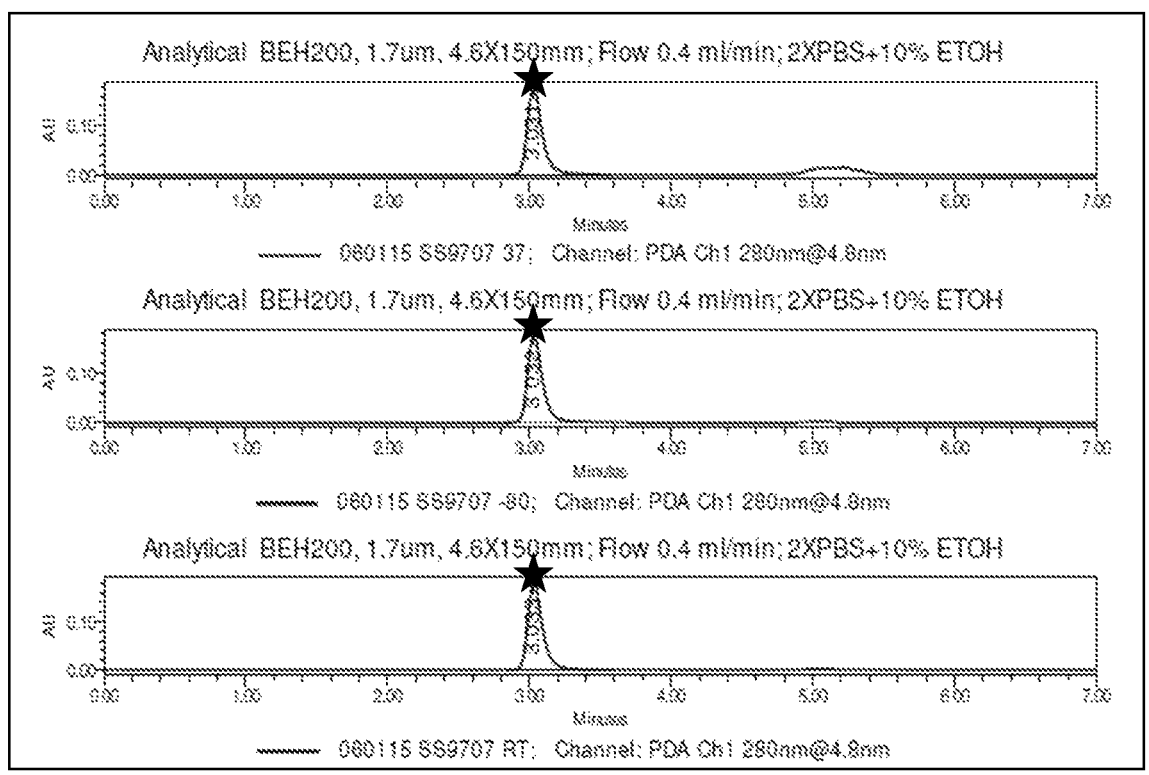
FIG. 3. IgG-scFv binding protein eluted from a temperature-responsive protein A chromatography column at 4° C. The figure shows SE-UPLC chromatograms from samples of the protein A eluate pool for an IgG-scFv binding protein. The binding protein was eluted from a temperature-responsive protein A chromatography column at 4° C. using an elution buffer having a pH of 7.2 and comprising 50 mM HEPES, 0.75 M NaCl, 0.5 M arginine, 0.5 M proline, 2.2 M sorbitol, and 4 M urea. The monomer peak is denoted by a black star. Each of the three panels is a separate experiment.

Varied volumes (10 ml-250 ml) of clarified and filtered culture medium containing the IgG-scFv binding protein were loaded on to TR-ProA column at a flow rate of 1 ml/min at 4° C. After washing with ten column volumes of Solution B, the bound IgG-scFv binding protein was eluted with five to ten column volumes of elution buffer at either 4° C. or room temperature. After the elution, the column was regenerated according to the manufacturer's instructions. A sample of the eluate pool was analyzed by SE-UPLC using a Superdex 200 analytical gel filtration column. The results of three independent experiments where the elution was performed at 4° C. are shown in FIG. 3. In one experiment, the protein was eluted with the elution buffer at 4° C. and stored for 7 days at 37° C. prior to SE-UPLC analysis (top panel in FIG. 3). In a second experiment, the protein was eluted with the elution buffer at 4° C. and stored for 7 days at −80° C. prior to SE-UPLC analysis (second panel in FIG. 3). In a third experiment, the protein was eluted with the elution buffer at 4° C. and stored for 7 days at room temperature prior to SE-UPLC analysis (third panel in FIG. 3). The results show that the IgG-scFv binding protein can be eluted in monomeric form from the TR-ProA resin at a low temperature with the elution buffer. Aggregation of the binding protein was completely eliminated as evidenced by the absence of peaks eluting from the gel filtration analytical column prior to the monomer peak (denoted by a black star). In addition, the elution conditions did not affect the subsequent temperature stability of the eluted IgG-scFv protein. No aggregation or degradation of the eluted protein was observed as a result of storing the eluted protein at various temperatures for 7 days.

Figure 4A:
FIG. 4A. SDS-PAGE of IgG-scFv binding protein during purification on temperature-responsive protein A chromatography column. The samples in each of the lanes on the gel are as follows: Stds=protein standards; Feed=sample of clarified cell culture supernatant prior to column loading; FT=sample of column flow through fraction; and Eluate=sample of eluate pool following elution of binding protein from column at room temperature with an elution buffer comprising 25 mM HEPES, 0.75 M NaCl, 0.5 M arginine, 0.5 M proline, 2.2 M sorbitol, and 4 M urea at pH 7.2.
Figure 4B:
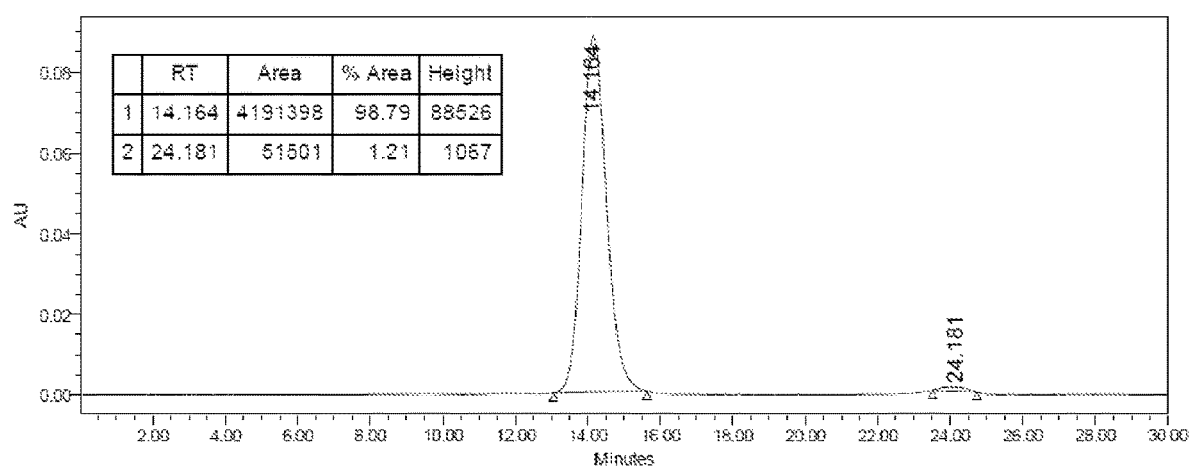
FIG. 4B. IgG-scFv binding protein eluted from a temperature-responsive protein A chromatography column at room temperature. The figure shows a SE-HPLC chromatogram of a sample of the temperature-responsive protein A eluate pool for an IgG-scFv binding protein. The bound protein was eluted from a temperature-responsive protein A chromatography column at room temperature using an elution buffer having a pH of 7.2 and comprising 25 mM HEPES, 0.75 M NaCl, 0.5 M arginine, 0.5 M proline, 2.2 M sorbitol, and 4 M urea. The peak with a retention time of about 14 minutes is the monomeric form of the binding protein. The inset provides retention times and peak area and height for each of the peaks shown on the chromatogram. Approximately 99% of the IgG-scFv binding protein present in the eluate pool is in monomeric form.

The purification of the IgG-scFv binding protein using the TR-ProA column was repeated using the same loading and elution conditions described above except that the elution was performed at room temperature rather than 4° C. Samples of the clarified culture medium prior to loading, the column flow-through solution during loading, and the eluate pool were analyzed by SDS-PAGE. The results of the SDS-PAGE analysis show that the IgG-scFv binding protein is enriched in the eluate pool and many contaminating proteins have been removed (FIG. 4A). A sample of the TR-ProA eluate pool was also analyzed by size exclusion—high performance liquid chromatography (SE-HPLC). As shown in the SE-HPLC chromatogram in FIG. 4B, 99% of the IgG-scFv binding protein present in the TR-ProA eluate pool is in monomeric form with no detectable aggregates.

Taken together, the results of the experiments in this example show that an Fc region-containing protein, such as a multiple-chain IgG-scFv binding protein, can be eluted from a temperature-responsive protein A resin at a neutral pH to reduce or eliminate aggregation of the protein that typically occurs with the low pH elution from conventional protein A chromatography. In addition, the results show that an elution buffer comprising a chaotropic agent, a sugar alcohol, and amino acids allows for the elution of the Fc region-containing protein from the temperature-responsive protein A resin without elevating the temperature above 35° C., which is typically required to elute proteins from the temperature-responsive protein A resin.

Example 2

Purification of a Single-Chain Bispecific Fv-Fc Binding Protein

This example describes the purification of a second type of Fc region-containing protein, a single-chain bispecific Fv-Fc binding protein, such as those described in WO2014144722, which is hereby incorporated by reference in its entirety, using either conventional protein A chromatography or the affinity chromatography method of the invention. The single-chain bispecific Fv-Fc binding protein comprises a first scFv fragment, which contains heavy and light chain variable domains from a first antibody, fused to a second scFv fragment, which contains heavy and light chain variable domains from a second antibody, and a Fc region, which is fused at its N-terminus through a peptide linker to the C-terminus of the first scFv fragment. The monomeric form of the bispecific Fv-Fc binding protein is shown in FIG. 5.

In a first series of experiments, the bispecific Fv-Fc binding protein was purified using conventional protein A affinity chromatography. Cell culture medium containing cells expressing the bispecific Fv-Fc binding protein was centrifuged at 600 rpm at 4° C. for 15 minutes. The supernatant was removed and filtered with a 0.22 micron filter. The clarified cell culture supernatant was then loaded on to a column containing MabSelect SuRe™ protein A resin (GE Healthcare) and washed according to the methods described in Example 1. After washing the column, the bound bispecific Fv-Fc binding protein was eluted at room temperature from the conventional protein A resin using either a 174 mM (1%) acetic acid solution at pH 2.7 or a 33 mM (0.06%) acetic acid solution at pH 3.7. Samples of the eluate pool were analyzed by SE-HPLC.

Figure 6A:
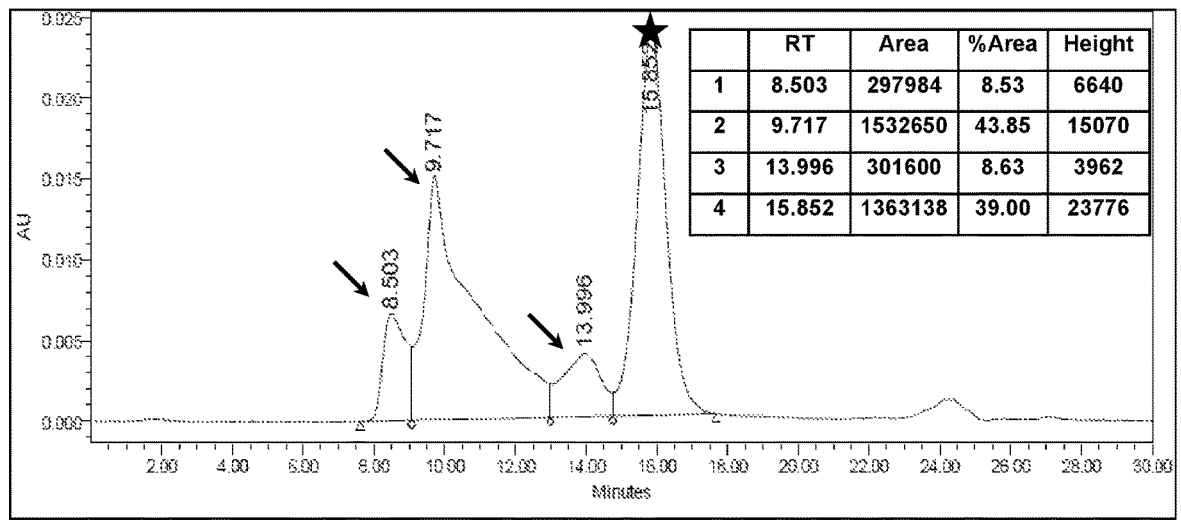
FIG. 6A. SE-HPLC chromatogram of bispecific Fv-Fc binding protein eluted from conventional protein A column using 174 mM acetic acid. The bispecific Fv-Fc binding protein was eluted from a conventional protein A chromatography column using 174 mM (1%) acetic acid, pH 2.7 at room temperature. The black arrows denote peaks corresponding to aggregates of the binding protein. The black star denotes the peak corresponding to the monomeric form of the binding protein. The inset provides retention times and peak area and height for each of the peaks shown on the chromatogram. Approximately 39% of the bispecific Fv-Fc binding protein present in the eluate pool is in monomeric form.
Figure 6B:
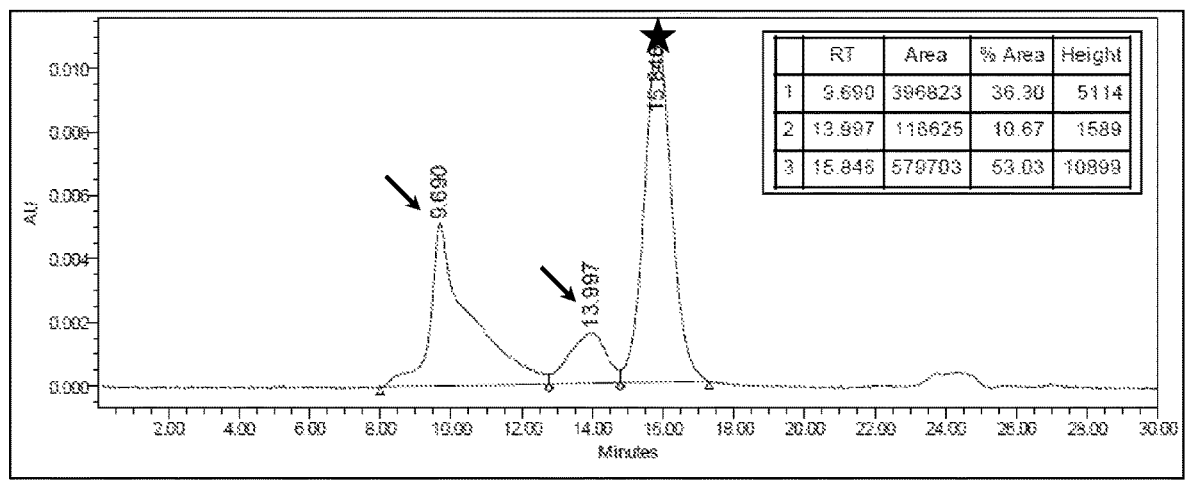
FIG. 6B. SE-HPLC chromatogram of bispecific Fv-Fc binding protein eluted from conventional protein A column using 33 mM acetic acid. The bispecific Fv-Fc binding protein was eluted from a conventional protein A chromatography column using 33 mM (0.06%) acetic acid, pH 3.7 at room temperature. The black arrows denote peaks corresponding to aggregates of the binding protein. The black star denotes the peak corresponding to the monomeric form of the binding protein. The inset provides retention times and peak area and height for each of the peaks shown on the chromatogram. Approximately 53% of the bispecific Fv-Fc binding protein present in the eluate pool is in monomeric form.

FIG. 6A shows the SE-HPLC profile of the eluate pool when the 174 mM (1%) acetic acid solution was used as the elution buffer, whereas FIG. 6B shows the SE-HPLC profile of the eluate pool when the lower concentration acetic acid solution was used as the elution buffer. Under both elution conditions, substantial aggregation of the bispecific Fv-Fc binding proteins was observed as evidenced by the multiple peaks (denoted by black arrows) with retention times shorter than the peak for the binding protein monomer (denoted by a black star). When 174 mM (1%) acetic acid solution was used as the elution buffer, only 39% of the bispecific Fv-Fc binding protein was recovered in monomeric form. Although reducing the concentration of the acetic acid in the elution buffer improved the recovery of the monomeric form of the binding protein, only 53% of the binding protein in the eluate pool was in monomeric form and significant aggregation was still observed. Thus, the bispecific Fv-Fc binding protein is particularly susceptible to aggregation under the typical low pH elution conditions required for conventional protein A chromatography.

In a second series of experiments, the bispecific Fv-Fc binding protein was purified using a temperature-responsive protein A resin (Byzen Pro®, Nomadic Bioscience Co., LTD.) and an elution buffer comprising a chaotropic agent, a sugar alcohol, an apolar amino acid, and a basic amino acid as described in Example 1. This elution buffer allowed for the elution of the binding protein from the temperature-responsive protein A (TR-ProA) resin without elevating the temperature of the column, a step which is usually required for elution of proteins from a temperature-responsive protein A resin. Specifically, clarified cell culture supernatant containing the bispecific Fv-Fc binding protein was loaded on to TR-ProA column at a flow rate of 1 ml/min and at a temperature of 4° C. After washing with ten column volumes of PBS containing 0.5 M NaCl, the bound bispecific Fv-Fc binding protein was eluted at room temperature with five to ten column volumes of either Elution Buffer 1 or Elution Buffer 2. Elution Buffer 1 contained 25 mM HEPES, 0.75 M NaCl, 0.5 M arginine, 0.5 M proline, 2.2 M sorbitol, and 2.5

M urea at pH 7.2. Elution Buffer 2 contained 25 mM HEPES, 0.75 M NaCl, 0.5 M arginine, 0.5 M proline, 2.2 M sorbitol, and 4 M urea at pH 7.2. Samples of the eluate pool were analyzed by SE-HPLC and SDS-PAGE.

Figure 7A:
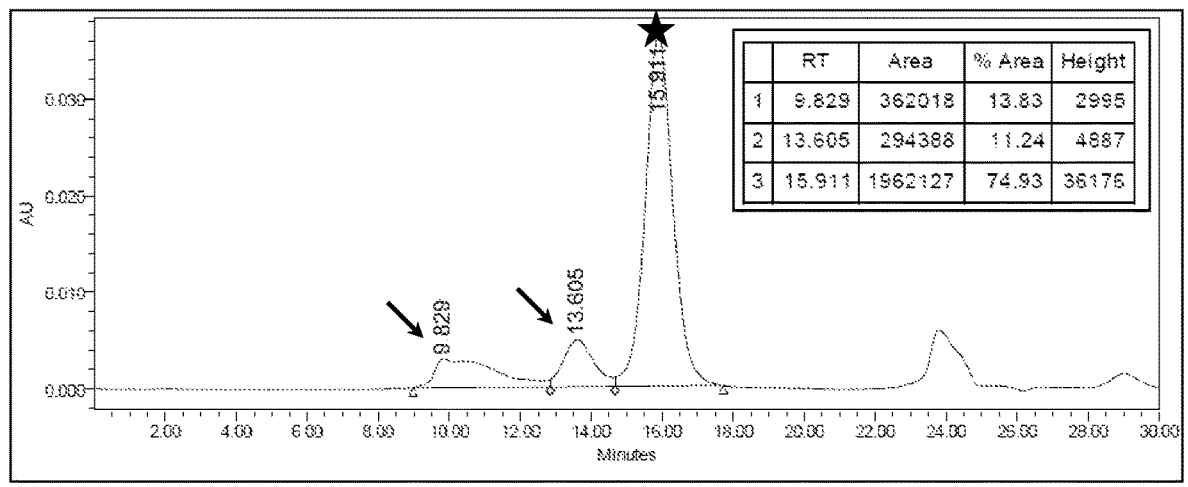
FIG. 7A. SE-HPLC chromatogram of a bispecific Fv-Fc binding protein eluted from temperature-responsive protein A column. The bispecific Fv-Fc binding protein was eluted from a temperature-responsive protein A chromatography column at room temperature using an elution buffer having a pH of 7.2 and comprising 25 mM HEPES, 0.75 M NaCl, 0.5 M arginine, 0.5 M proline, 2.2 M sorbitol, and 2.5 M urea. The inset provides retention times and peak area and height for peaks shown on the chromatogram. The black arrows denote peaks corresponding to aggregates of the binding protein. The peak with a retention time of about 15.9 minutes corresponds to the monomeric form of the Fv-Fc binding protein and is annotated with a black star. Approximately 75% of the bispecific Fv-Fc binding protein present in the eluate pool is in monomeric form.
Figure 7B:
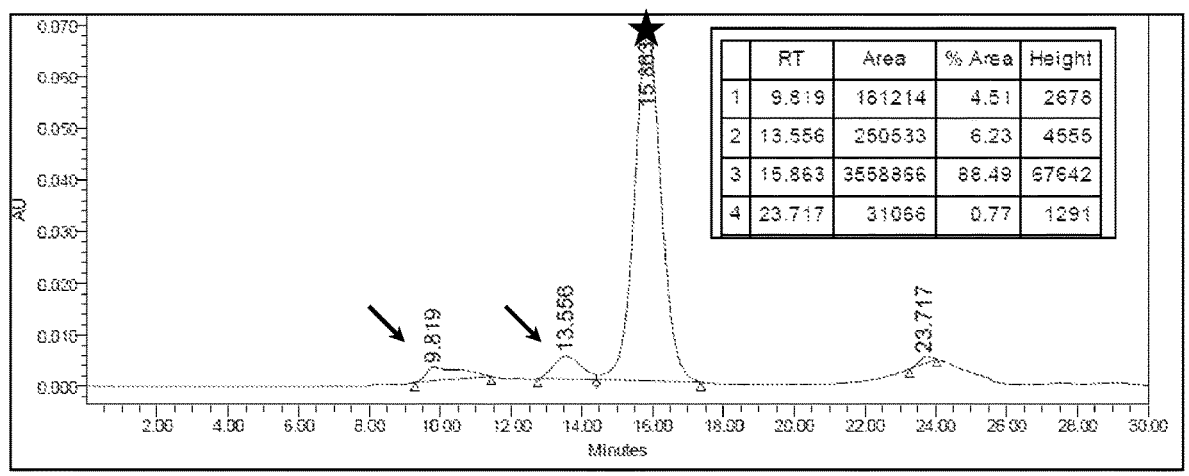
FIG. 7B. SE-HPLC chromatogram of a bispecific Fv-Fc binding protein eluted from temperature-responsive protein A column. The bispecific Fv-Fc binding protein was eluted from a temperature-responsive protein A chromatography column at room temperature using an elution buffer having a pH of 7.2 and comprising 25 mM HEPES, 0.75 M NaCl, 0.5 M arginine, 0.5 M proline, 2.2 M sorbitol, and 4 M urea. The inset provides retention times and peak area and height for each of the peaks shown on the chromatogram. The black arrows denote peaks corresponding to aggregates of the binding protein. The peak with a retention time of about 15.9 minutes corresponds to the monomeric form of the Fv-Fc binding protein and is annotated with a black star. Approximately 88% of the bispecific Fv-Fc binding protein present in the eluate pool is in monomeric form.
Figure 7C:
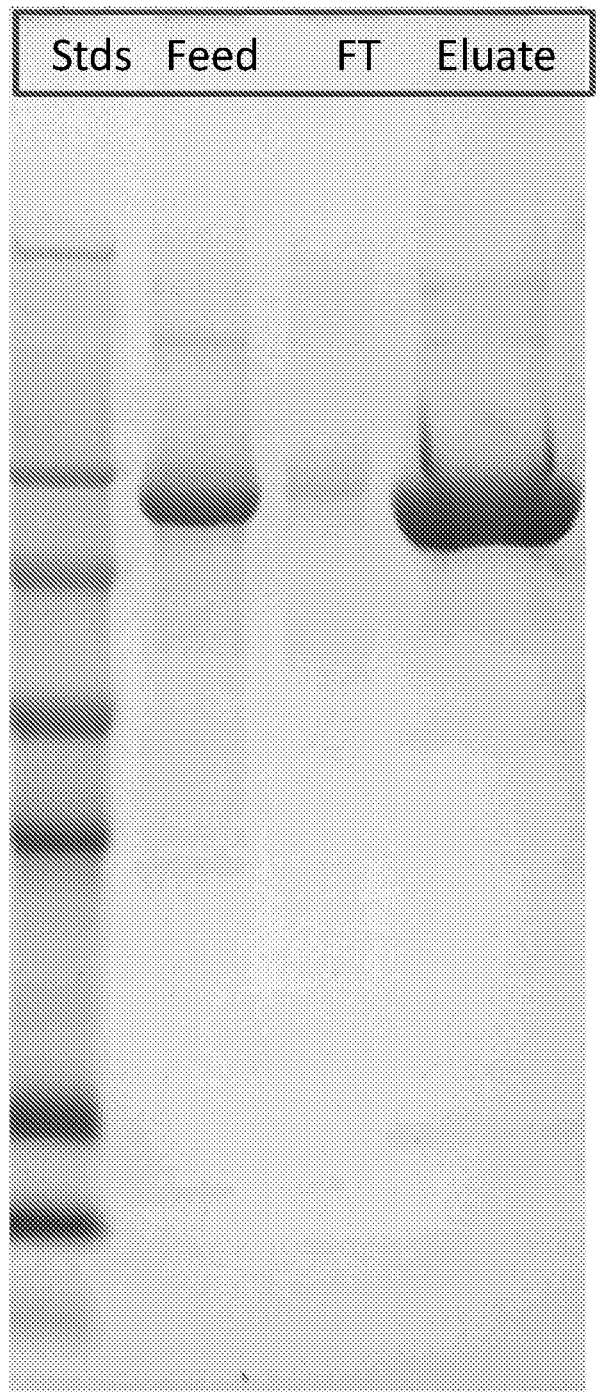
FIG. 7C. SDS-PAGE of bispecific Fv-Fc eluate from temperature-responsive protein A column buffer. Different samples were taken during the purification of a bispecific Fv-Fc binding protein with a temperature-responsive protein A chromatography column. The samples in each of the lanes on the gel are as follows: Stds=protein standards; Feed=sample of clarified cell culture supernatant prior to column loading; FT=sample of column flow through fraction; and Eluate=sample of eluate pool following elution of binding protein from column at room temperature with an elution buffer comprising 25 mM HEPES, 0.75 M NaCl, 0.5 M arginine, 0.5 M proline, 2.2 M sorbitol, and 4 M urea at pH 7.2.

FIG. 7A shows the SE-HPLC profile of the eluate pool resulting from elution of the binding protein with Elution Buffer 1 at room temperature, whereas FIG. 7B shows the SE-HPLC profile of the eluate pool resulting from elution of the binding protein with Elution Buffer 2 at room temperature. As can be seen from both profiles, similar to the results obtained with the IgG-scFv binding protein described in Example 1, the bispecific Fv-Fc binding protein can be eluted in substantially monomeric form from the TR-ProA resin with both elution buffers at a temperature below 30° C. Under both elution conditions, aggregation of the Fv-Fc binding protein was significantly reduced as compared to the aggregation resulting from elution from a conventional protein A chromatography column with a low pH buffer (compare peaks denoted by black arrows in FIGS. 6A and 6B with those in FIGS. 7A and 7B). Moreover, comparison of the profile in FIG. 7A with the profile in FIG. 7B, shows that increasing the concentration of the chaotropic agent (e.g. urea) in the elution buffer from 2.5 M to 4 M, increased the percentage of monomeric Fv-Fc binding protein recovered in the eluate pool from 75% to 88%, and further reduced the amount of aggregated binding protein present in the eluate pool. Results of the SDS-PAGE analysis of samples prior to, during, and after purification of the bispecific Fv-Fc binding protein with the TR-ProA resin and Elution Buffer 2 are shown in FIG. 7C. The results show that Fv-Fc binding protein is enriched in the eluate pool.

The results of the experiments described in this example show that single-chain Fc fusion proteins, such as bispecific Fv-Fc binding proteins, have a tendency to aggregate during the low pH conditions required to elute bound proteins from a conventional protein A resin. Such aggregation of the binding protein is substantially reduced by employing a temperature-responsive protein A resin and an elution buffer comprising a chaotropic agent, a sugar alcohol, an apolar amino acid, and a basic amino acid. Importantly, the composition of the elution buffer enables the binding protein to be removed from the temperature-responsive protein A resin in substantially monomeric form without elevating the temperature above 35° C.

Example 3

Buffers for Elution of Fc Region-Containing Proteins from Temperature-Responsive Protein A Resin Experiments described in this example were designed to explore the ability of different elution buffers to remove bound Fc region-containing proteins from a temperature-responsive protein A (TR-ProA) resin without elevating the temperature of the resin above room temperature. Clarified cell culture supernatant from cells expressing either an IgG-scFv binding protein as described in Example 1 or a single-chain bispecific Fv-Fc binding protein as described in Example 2, was loaded onto a column of temperature-responsive protein A resin (Byzen Pro®, Nomadic Bioscience Co., LTD.) at 4° C. and washed with a PBS solution containing 0.5 M NaCl. The bound binding protein was eluted from the column at 4° C. using one of the elution buffers listed in Table 2 below. The percentage of the binding protein recovered as a monomer in the eluate pool was determined using SE-HPLC. The results are shown in Table 2 below.

TABLE 2

Recovery of Monomeric Binding Protein Following Elution from TR-ProA Resin with Different Elution Buffers

| Elution Buffer No. | Elution Buffer Composition | % Binding Protein Monomer in Eluate Pool |
| --- | --- | --- |
| 1 | 25 mM HEPES, pH 7.2 | 0% |
| 2 | 25 mM HEPES, 0.75M NaCl, pH 7.2 | 5% |
| 3 | 25 mM HEPES, 0.75M NaCl, 0.5M arginine, 0.05M glutamic acid, 2.2M sorbitol, pH 7.2 | 20% |
| 4 | 25 mM HEPES, 0.75M NaCl, 0.5M arginine, pH 7.2 | 35% |
| 5 | 25 mM HEPES, 0.75M NaCl, 0.5M arginine, 0.5M proline, 2.2M sorbitol, pH 7.2 | 40% |
| 6 | 25 mM HEPES, 0.75M NaCl, 0.5M arginine, 0.5M proline, 2.2M sorbitol, 4M urea, pH 7.2 | >90% |
| 7 | 0.1M Trizma base, 0.1M ascorbic acid, 0.5M arginine, 0.5M proline, 0.3M NaCl, pH 7.2 | 0% |
| 8 | 0.1M Trizma base, 0.1M ascorbic acid, 2.2M sorbitol, 0.5M NaCl, pH 7.2 | 10% |
| 9 | 0.1M Trizma base, 0.174M acetic acid, 2M proline, 0.6M NaCl, pH 6.8 | 2% |
| 10 | 0.1M Trizma base, 0.174M acetic acid, 0.5M tyrosine, 0.6M NaCl, pH 7.0 | 12% |
| 11 | 0.1M ascorbic acid, 2M proline, 0.7M NaCl, pH 6.9 | 20% |
| 12 | 0.1M acetic acid, 2M proline, 0.5M arginine, 0.6M NaCl, pH 7.0 | 14% |
| 13 | 0.174M acetic acid, 2M proline, 0.15M Trizma base, 0.5M NaCl, pH 6.8 | 8% |
| 14 | 0.1M ascorbic acid, 0.1M Bis-Tris, 1M NaCl, pH 7.2 | 0% |
| 15 | 0.1M acetic acid, 0.1M Trizma base, 0.5M proline, 0.5M arginine, 0.75M NaCl, pH 6.8 | 2% |

The results show inclusion of a chaotropic agent (e.g. urea) significantly enhances elution and recovery of the monomeric form of the binding protein.

Example 4

Purification of a Monoclonal Antibody

Figures 8A, 8B:
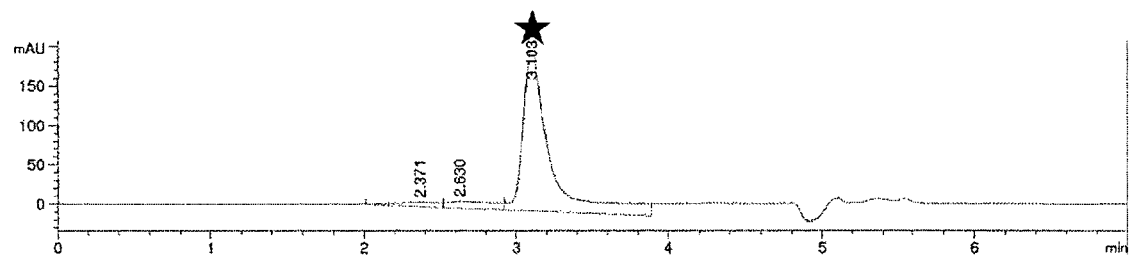
FIG. 8A. SE-HPLC chromatogram of a monoclonal antibody eluted from temperature-responsive protein A column at 4° C. The antibody was eluted from a temperature-responsive protein A chromatography column at 4° C. using an elution buffer having a pH of 7.2 and comprising 20 mM HEPES, 2 M guanidinium chloride, and 2.2 M sorbitol. The peak corresponding to the monomeric form of the antibody is denoted with a black star.
FIG. 8B. Table summarizing the characteristics of the peaks shown in the chromatogram in FIG. 8A. Nearly 90% of the monoclonal antibody was recovered in monomeric form in the eluate pool.

This example describes the purification of a monoclonal antibody using temperature responsive protein A resin. Clarified cell culture supernatant from cells expressing the antibody was loaded onto a column of temperature-responsive protein A resin (Byzen Pro®, Nomadic Bioscience Co., LTD.) at 4° C. and washed with a PBS solution containing 0.5 M NaCl. The bound antibody was eluted from the column at 4° C. with an elution buffer comprising 20 mM HEPES, 2 M guanidinium chloride, and 2.2 M sorbitol and having a pH of 7.2. A sample of the eluate pool was analyzed by SE-HPLC and the results are shown in FIGS. 8A and 8B. The monoclonal antibody could be eluted from the temperature responsive protein A resin at a low temperature using an elution buffer comprising only a chaotropic agent (e.g. guanidinium chloride) and a sugar alcohol (sorbitol) in a molar concentration ratio of about 0.9. Nearly 90% of the antibody was recovered in monomeric form in the eluate pool.

Example 5

Separation of Half Antibodies from Full Antibodies

Half antibodies result from incompletion of the assembly or disruption of the interaction between the two heavy chain polypeptides of an antibody (e.g. disruption of inter-polypeptide disulfide bond formation between the hinge regions of the two heavy chains). Half antibodies generally are comprised of a single light chain polypeptide and a single heavy chain polypeptide. Removal of half antibodies from preparations containing the desired full antibodies is important for several reasons. The presence of half antibodies decreases the full antibody product concentration, reduces dose reproducibility, and decreases product homogeneity. In addition, half antibodies can compete with the full antibodies for binding to targets and may reduce the efficacy of the full antibodies.

Separating half antibodies from full antibodies can be challenging because half antibodies have similar properties as the full antibodies. For instance, both half antibodies and full antibodies contain a similar Fc region and thus, cannot be effectively separated using protein A affinity chromatography. Half antibodies have similar isoelectric points, axial ratios, and hydrodynamic radii as full antibodies and thus, separation methods based on these characteristics are generally not suitable. In addition, half antibodies tend to self-associate and associate with full antibodies making their removal more difficult.

The presence of half antibodies is often observed in recombinant preparations of antibodies, particularly heterodimeric antibodies, even after purification by conventional protein A affinity chromatography (FIGS. 9A and 9B). A heterodimeric antibody is an antibody that comprises a light chain and heavy chain from a first antibody that binds to a first target and a light chain and heavy chain from a second antibody that binds to a second target. Thus, two species of half antibodies can result from recombinant production of these bispecific heterodimeric antibodies: one half antibody that binds to the first target and another half antibody that binds to a second target. The presence and levels of half antibodies can vary from different lots of recombinant production of the heterodimeric antibodies (FIGS. 9A and 9B), and the overall yield of the fully assembled heterodimeric antibodies can be quite low due to the number and nature of the steps required to remove the half antibodies (data not shown).

Figure 10A:
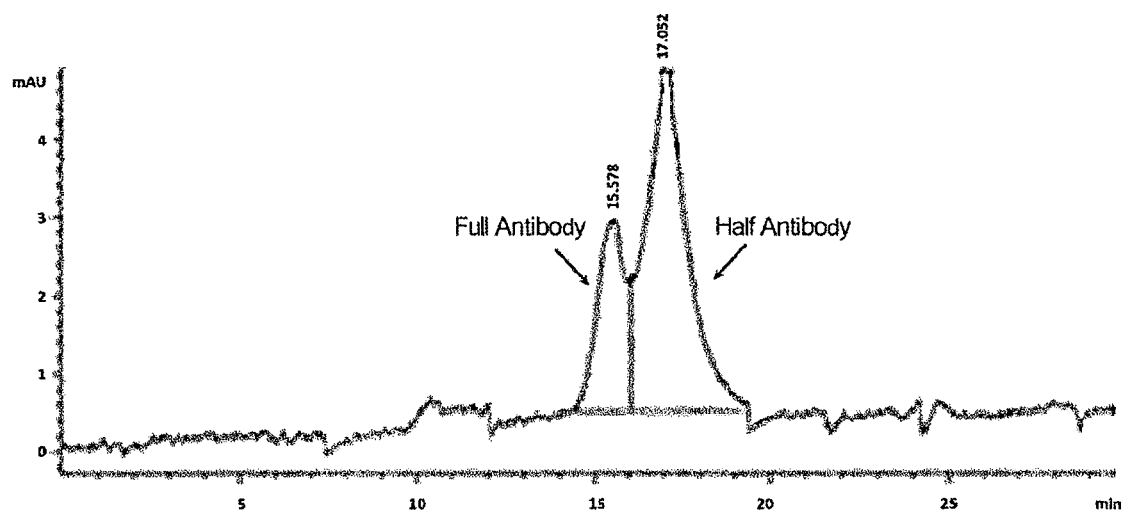
FIG. 10A. The figure shows a SE-HPLC chromatogram for a sample of the conventional protein A eluate pool of a bispecific heterodimeric antibody ("heterodimeric antibody A"). The fully assembled heterodimeric antibody ("Full Antibody") elutes before the half antibody on the analytical size exclusion column. The table beneath the chromatogram provides retention times and peak area, width, and height for the two peaks shown on the chromatogram. Approximately 72% of half antibody is present in the eluate pool.
Figure 10B:
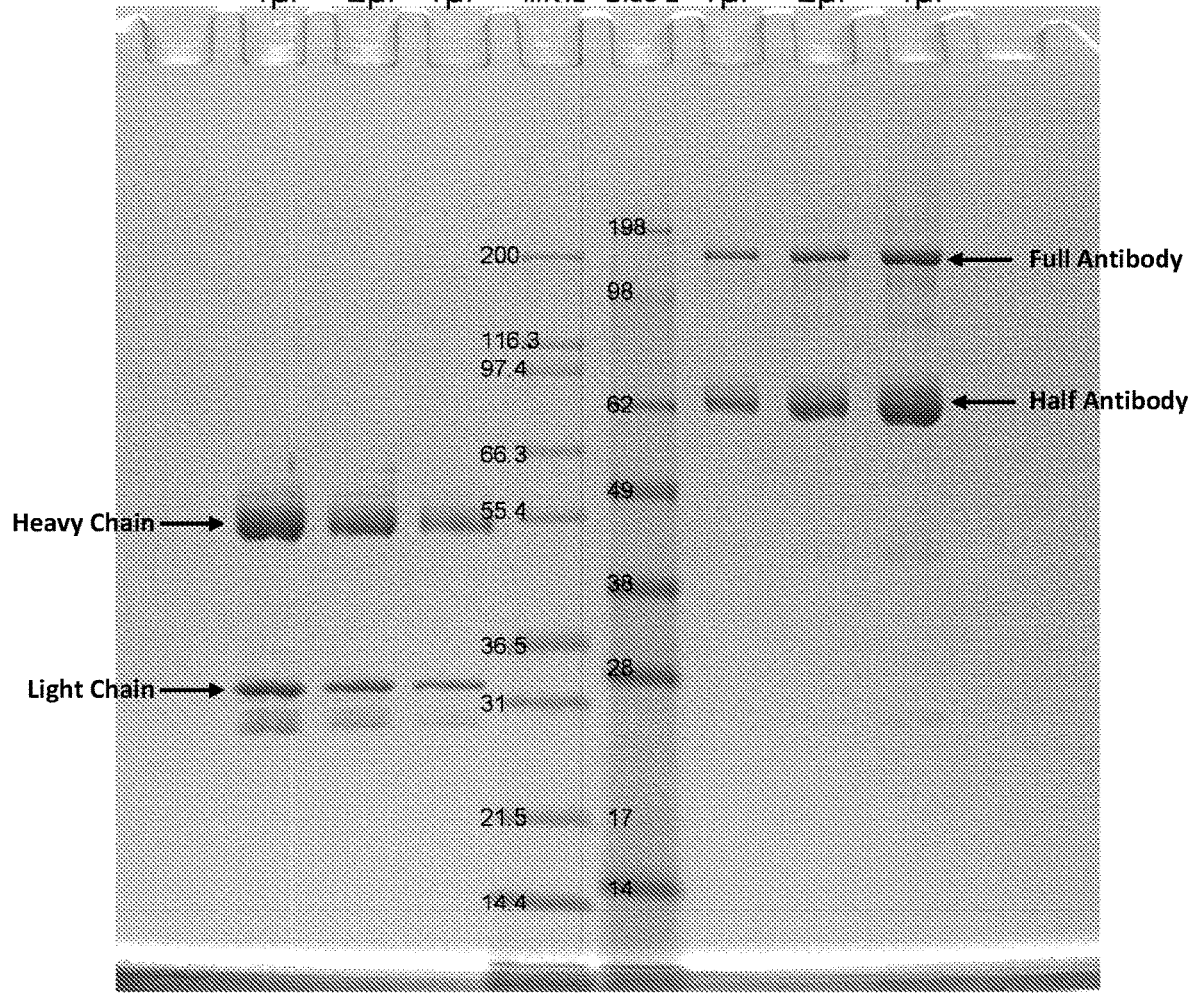
FIG. 10B. SDS-PAGE analysis of samples from the conventional protein A eluate pool of a bispecific heterodimeric antibody ("heterodimeric antibody A"). The indicated sample volumes in reducing (left side of gel) or non-reducing (right side of gel) conditions were loaded onto a 4-20% gradient Tris-Glycine SDS gel. Protein standards were loaded into the middle lanes. A significant amount of half antibody is present following purification by conventional protein A chromatography.

Cell culture medium containing cells expressing a bispecific heterodimeric antibody ("heterodimeric antibody A") was subjected to low speed centrifugation (600 rpm) at 4° C. for 15 minutes in order to sediment the cells and cell debris. The resulting clarified supernatant solution was passed through a 0.22 micron filter to remove fine particulates and soluble aggregates. The clarified and filtered solution was loaded on to a column containing MabSelect SuRe™ resin (GE Healthcare) at a flow rate of 1 ml/min and at a temperature of 4° C. After washing the column with a phosphate buffered saline solution containing 0.5 M NaCl at pH 7.2, the bound antibodies were eluted from the conventional protein A resin using a 174 mM (1%) acetic acid solution at pH 2.7 and at a temperature of 4° C. A sample of the eluate pool was analyzed by SE-HPLC (FIG. 10A) and SDS-PAGE (FIG. 10B). As shown by the SE-HPLC and SDS-PAGE analyses, the protein A eluate pool contained a significant amount (about 72%) of half antibody.

Figure 11:
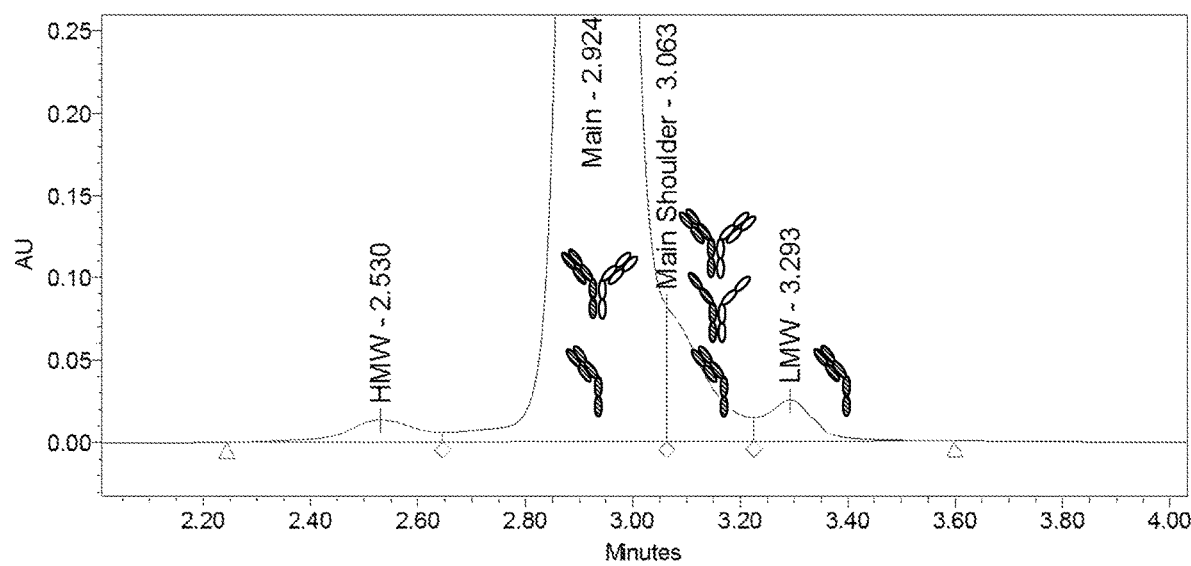
FIG. 11. Preparative SEC chromatogram of a bispecific heterodimeric antibody ("heterodimeric antibody A") preparation. The bispecific heterodimeric antibody preparation was subject to preparative SEC gel filtration using a mobile phase comprising PBS, pH 7.0. SEC operated under conventional conditions is not able to separate half antibodies from the fully assembled heterodimeric antibodies and other incomplete fragments.

In an effort to remove the half antibodies that remained in the protein A eluate pool, a preparative size exclusion chromatography (SEC) step operated under conventional conditions was evaluated. Specifically, the protein A eluate pool was loaded onto a Superdex 200 preparative gel filtration column using a mobile phase comprising phosphate buffered saline at a pH of 7.0 at a flow rate of 1 ml/min. As shown in FIG. 11, SEC operated under these conditions was not capable of separating the fully assembled heterodimeric antibodies from the half antibodies. Decreasing the flow rate through the preparative SEC column of the PBS-containing mobile phase to rates as low as 0.01 ml/min did not improve the separation (data not shown).

Figures 13A, 13B:
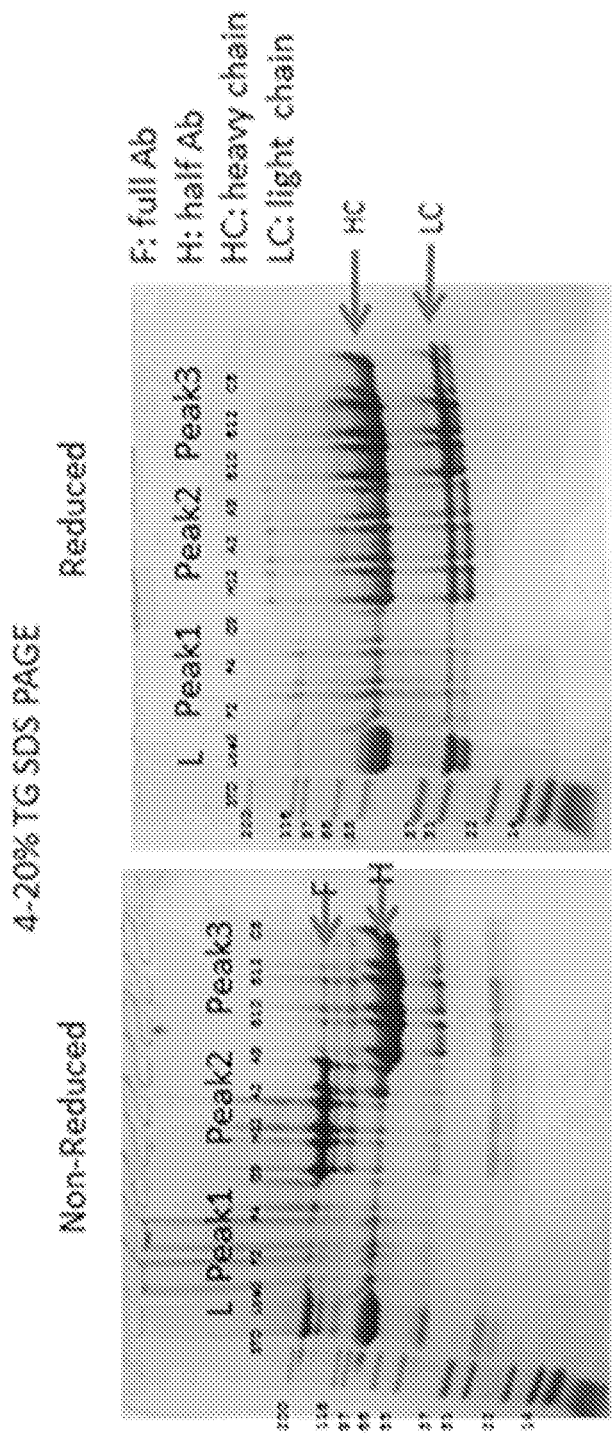
FIGS. 13A and 13B. SDS-PAGE analysis of elution fractions from SEC, the profile of which is shown in FIG. 12. Fractions were collected through each of the three peaks. "L"=load material prior to SEC. Samples were loaded onto a 4-20% gradient Tris-Glycine SDS gel in either non-reducing (FIG. 13A) or reducing (FIG. 13B) conditions. Peak 2 primarily comprises fully assembled antibodies ("F"), whereas peak 3 primarily comprises the half antibodies ("H"). Peak 1 corresponds to higher molecular weight aggregates. SEC using a mobile phase comprising 50 mM HEPES, 0.75 M NaCl, 0.5 M arginine, 0.5 M proline, 2.2 M sorbitol, and 4 M urea at pH 7.2 effectively separated the fully assembled heterodimeric antibodies from the half antibodies.
Figure 14A:
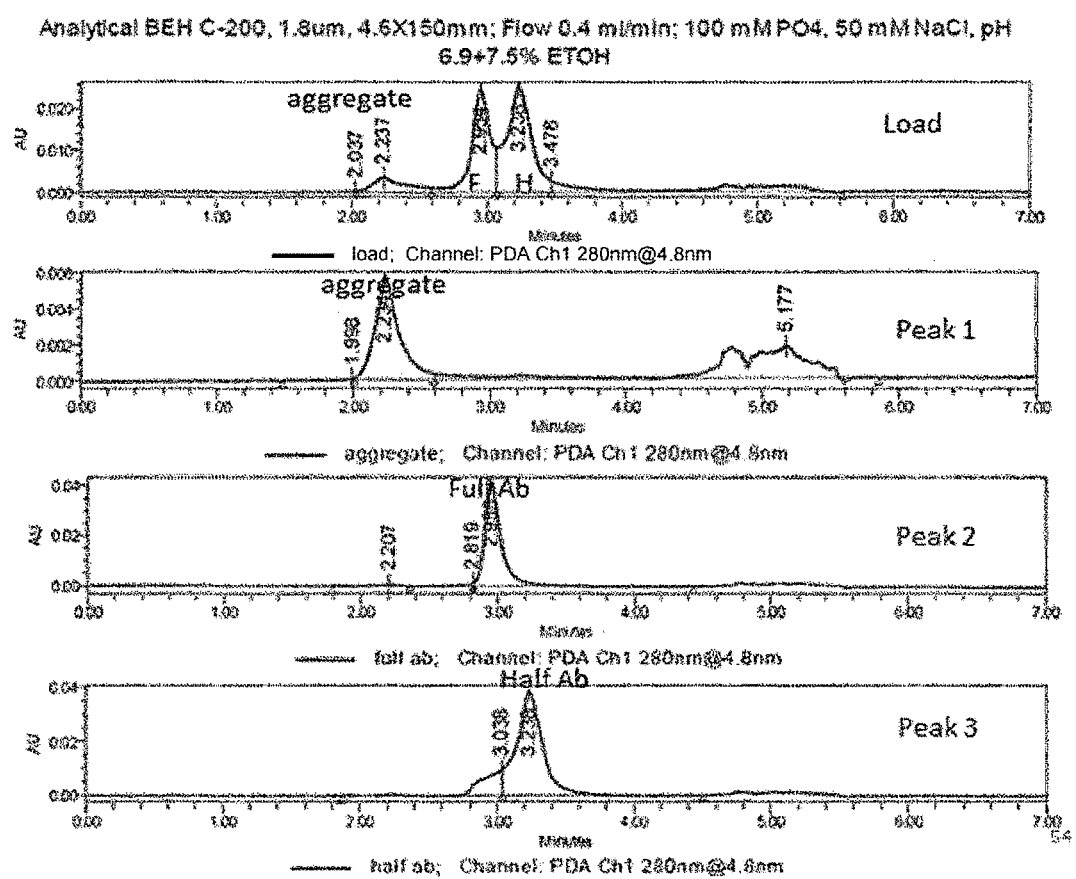
FIG. 14A. The figure shows analytical SE-HPLC chromatograms from samples of load material comprising a bispecific heterodimeric antibody before SEC and elution fractions from each of the three primary protein peaks during the SEC shown in FIG. 12. The eluate pool from a conventional protein A chromatography comprising a bispecific heterodimeric antibody ("heterodimeric antibody A") was loaded onto a preparative SEC gel filtration column (2×80 ml Superdex 200). The SEC was conducted with a mobile phase comprising 50 mM HEPES, 0.75 M NaCl, 0.5 M arginine, 0.5 M proline, 2.2 M sorbitol, and 4 M urea at pH 7.2 at a flow rate of 0.02 ml/min. The fully assembled heterodimeric antibody elutes primarily in peak 2, whereas the half antibodies primarily elute in peak 3. The higher molecular weight aggregates elute in peak 1. SEC operated with this mobile phase can effectively separate the fully assembled heterodimeric antibodies from the half antibody contaminants.
Figure 14B:
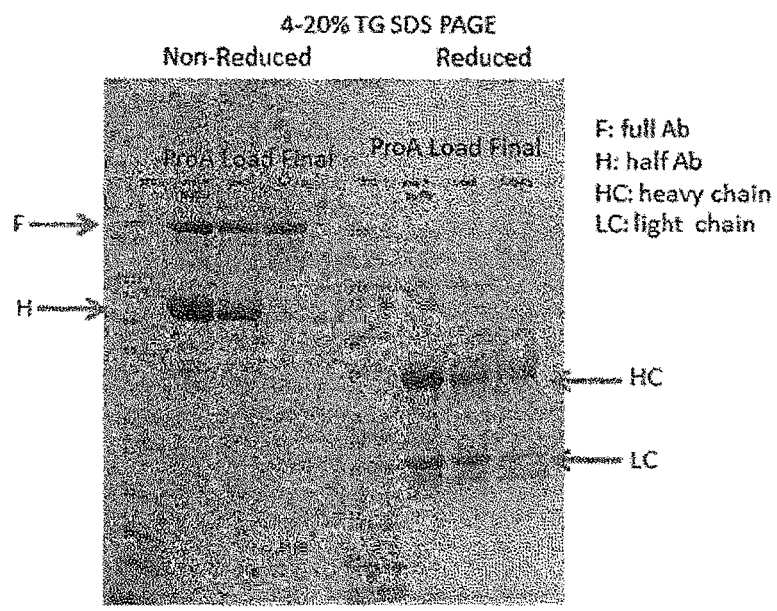
FIG. 14B. SDS-PAGE analysis of samples of recombinant heterodimeric antibody from the conventional protein A eluate pool, the load material before SEC, and the final pool following SEC. Samples were loaded onto a 4-20% gradient Tris-Glycine SDS gel in either non-reducing (left side of gel) or reducing (right side of gel) conditions.
Figure 14C:
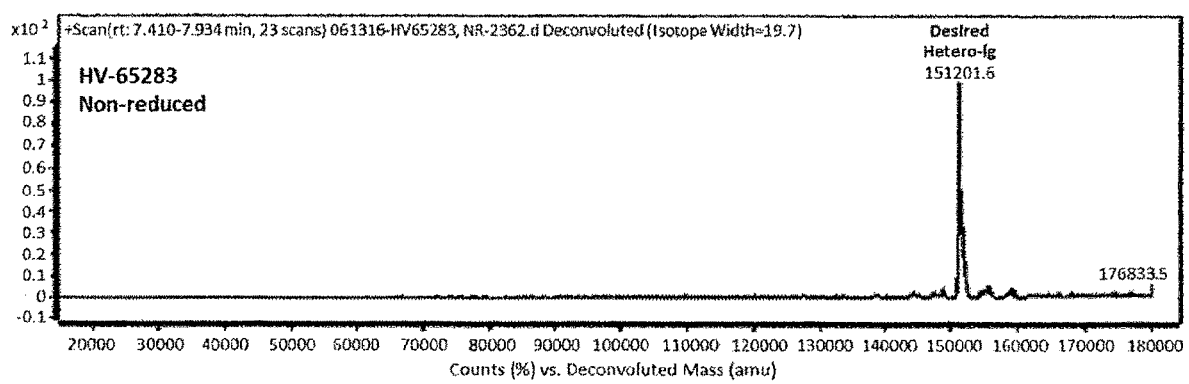
FIG. 14C. LCMS chromatogram of a recombinant bispecific heterodimeric antibody following SEC purification with a mobile phase comprising 50 mM HEPES, 0.75 M NaCl, 0.5 M arginine, 0.5 M proline, 2.2 M sorbitol, and 4 M urea at pH 7.2. Only the fully assembled heterodimeric antibody is detectable. Neither of the two species of half antibodies are detectable. SEC efficiently removes half antibody contaminants. Compare to FIGS. 9A and 9B.

The experiment was repeated, but the conventional mobile phase comprising PBS was replaced with a mobile phase with a similar composition as the unique elution buffer described in Example 1. The protein A eluate pool comprising the fully assembled heterodimeric antibody and half antibodies was loaded onto a Superdex 200 preparative gel filtration column (2×80 ml) using a mobile phase comprising 50 mM HEPES, 0.75 M NaCl, 0.5 M arginine, 0.5 M proline, 2.2 M sorbitol, and 4 M urea at pH 7.2. Three distinct protein peaks were observed during elution from the preparative gel filtration column (FIG. 12). Various fractions were collected during the elution and analyzed by analytical SE-HPLC and SDS-PAGE. SDS-PAGE analysis revealed that peak 2 largely comprised fully assembled antibodies, whereas peak 3 was mostly comprised of half antibodies (FIGS. 13A and 13B). Peak 1 corresponded to higher molecular weight aggregates. Surprisingly, the use of this unique mobile phase in SEC allowed for the separation of the half antibodies from the fully assembled antibodies as well as from higher molecular weight aggregates (FIGS. 14A-14C).

Figure 15A:
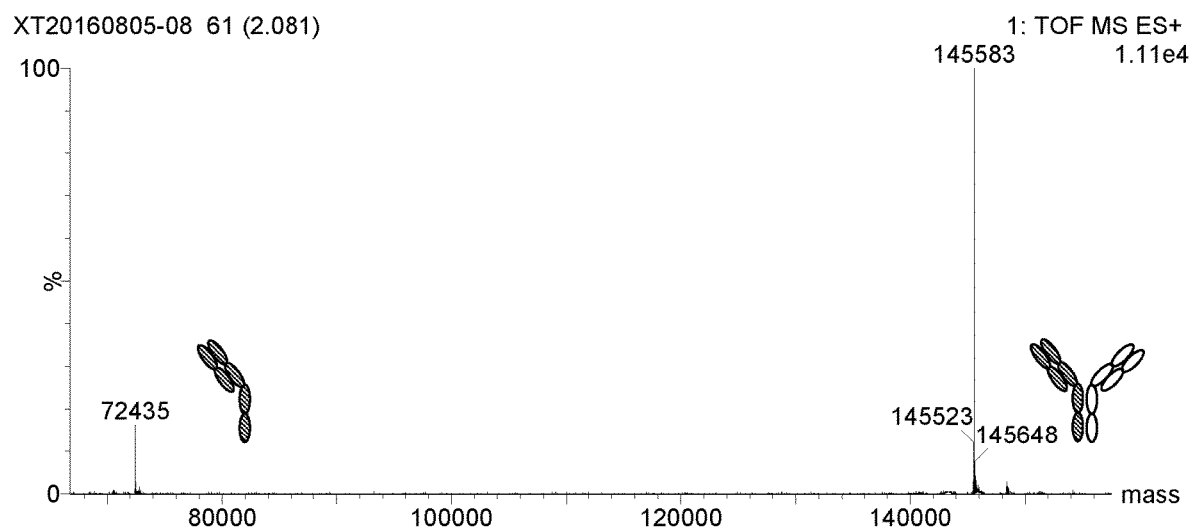
FIGS. 15A and 15B. The figures depict LCMS chromatograms of recombinant bispecific heterodimeric antibody B before (FIG. 15A) and after (FIG. 15B) purification with SEC using a mobile phase comprising 50 mM HEPES, 0.75 M NaCl, 0.5 M arginine, 0.5 M proline, 2.2 M sorbitol, and 4 M urea at pH 7.2. Before SEC purification, the preparation contains both fully assembled antibodies as well as half antibodies. After SEC purification, no half antibodies can be detected.
Figure 15B:
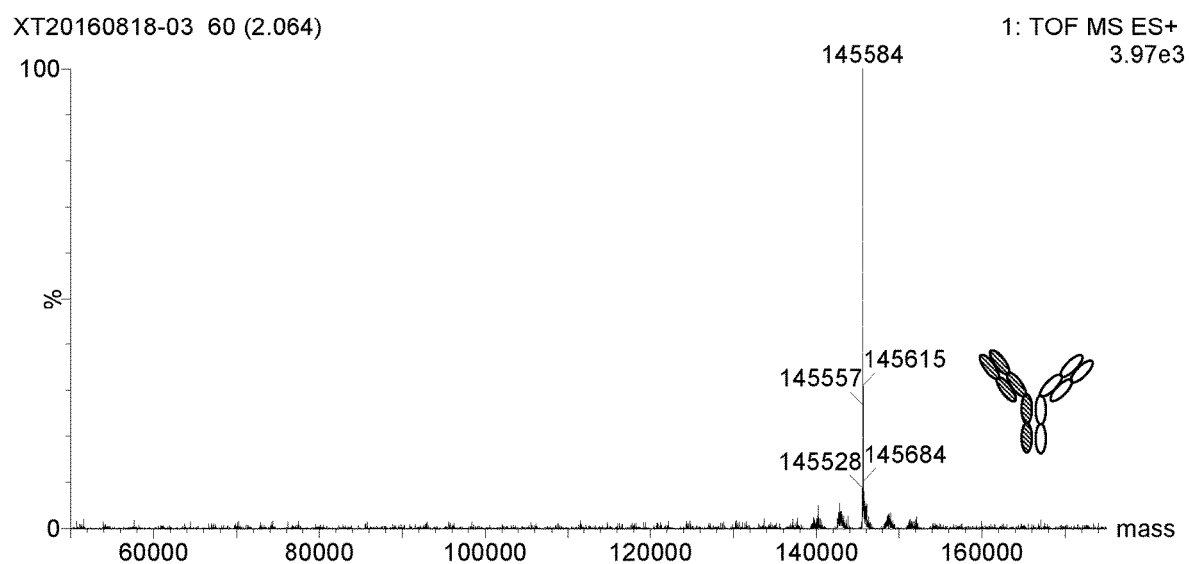
Figure 16A:
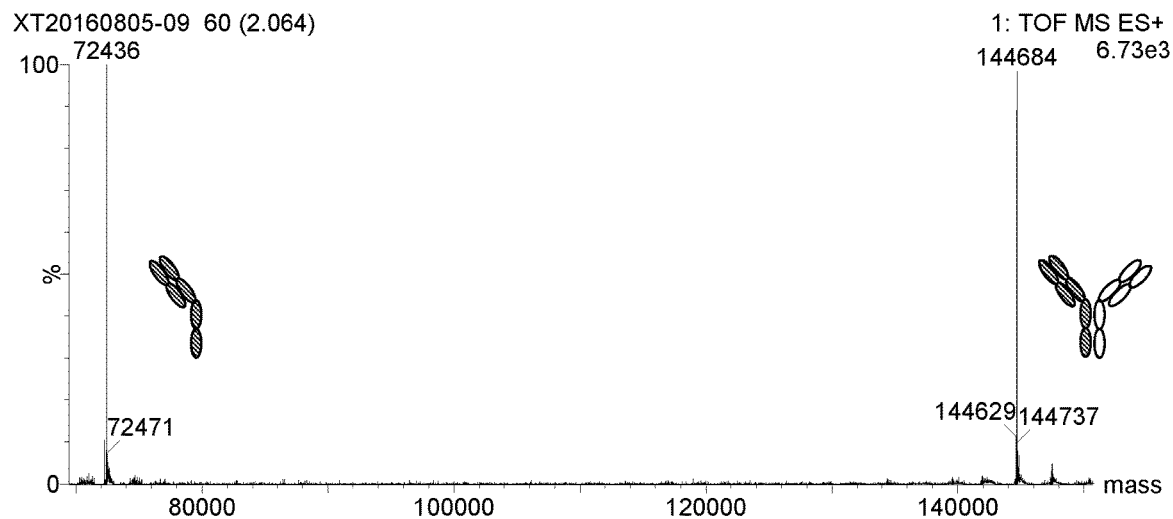
FIGS. 16A and 16B. The figures depict LCMS chromatograms of recombinant bispecific heterodimeric antibody C before (FIG. 16A) and after (FIG. 16B) purification with SEC using a mobile phase comprising 50 mM HEPES, 0.75 M NaCl, 0.5 M arginine, 0.5 M proline, 2.2 M sorbitol, and 4 M urea at pH 7.2. Before SEC purification, the preparation contains both fully assembled antibodies as well as half antibodies. After SEC purification, no half antibodies can be detected.
Figure 16B:
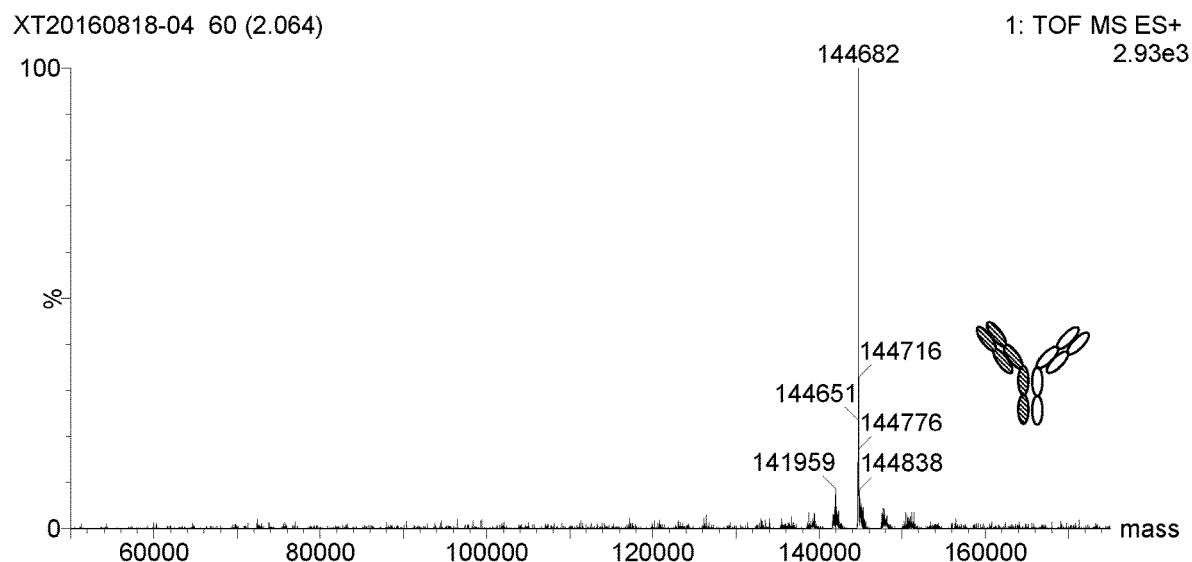
Figure 17A:
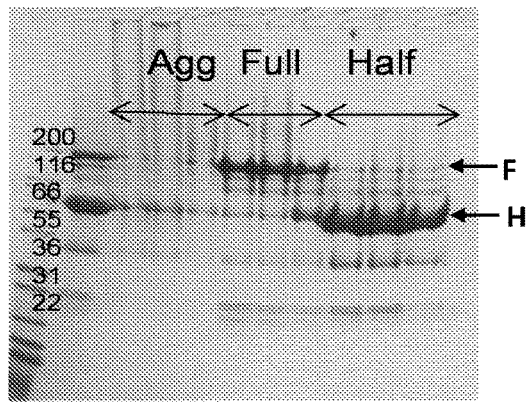
FIGS. 17A-17F. SDS-PAGE analysis of a recombinant bispecific heterodimeric antibody from elution fractions from a preparative SEC gel filtration column using a mobile phase comprising 50 mM HEPES, 0.75 M NaCl, 0.5 M arginine, 0.5 M proline, 2.2 M sorbitol, and 4 M urea at pH 7.2. The SEC was conducted at different flow rates: 0.02 ml/min (FIG. 17A), 0.04 ml/min (FIG. 17B), 0.06 ml/min (FIG. 17C), 0.08 ml/min (FIG. 17D), 0.1 ml/min (FIG. 17E), and 0.2 ml/min (FIG. 17F). "F"=fully assembled heterodimeric antibodies. "H"=half antibodies. Samples were loaded onto a 4-20% gradient Tris-Glycine SDS gel in non-reducing conditions. The half antibody separation efficiency decreases with increasing flow rate.
Figure 17B:
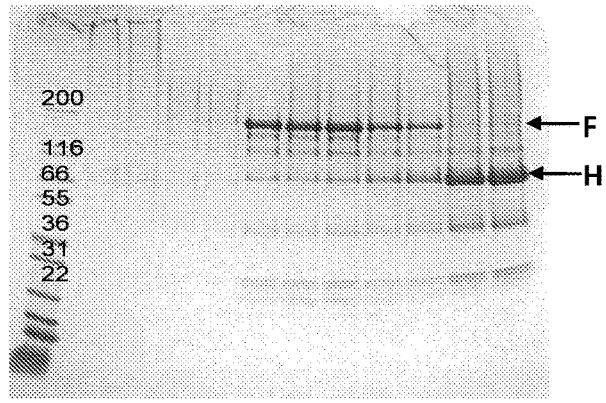
Figure 17C:
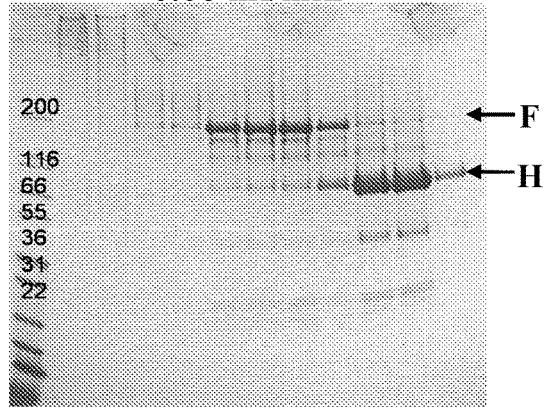
Figure 17D:
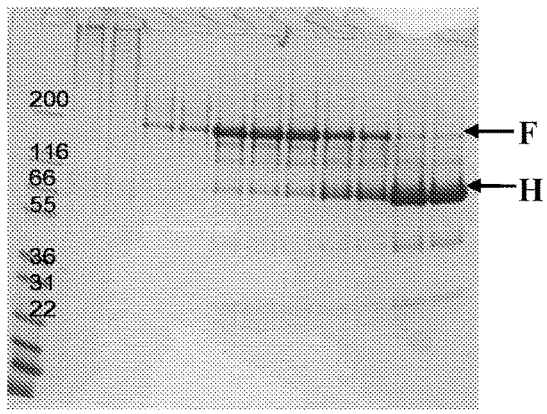
Figure 17E:
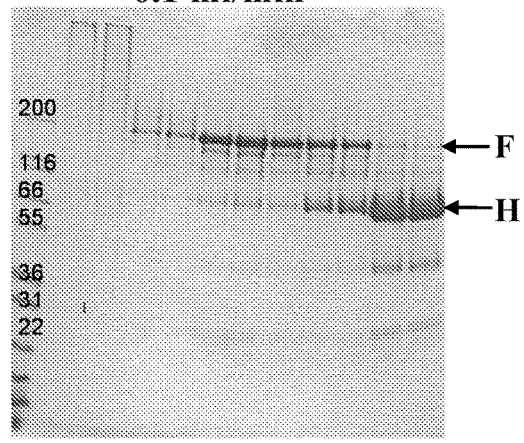
Figure 17F:
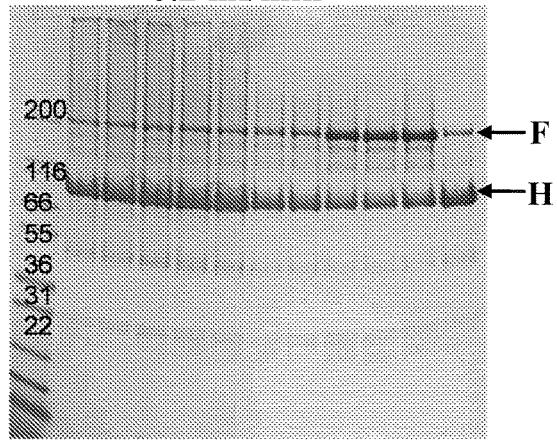

The preparative SEC process using the unique mobile phase described above was repeated with two other bispecific heterodimeric antibodies having specificity for different target antigens. Preparations of both heterodimeric antibody B and heterodimeric antibody C prior to SEC purification contained half antibody contaminants (FIGS. 15A and 16A). However, following purification with SEC using a mobile phase comprising 50 mM HEPES, 0.75 M NaCl, 0.5 M arginine, 0.5 M proline, 2.2 M sorbitol, and 4 M urea at pH 7.2, the fully assembled heterodimeric antibodies could be separated from the half antibodies such that only the desired fully assembled heterodimeric antibodies remained (FIGS. 15B and 16B).

In another series of experiments, the effect of flow rate on the efficiency of half antibody separation using SEC was evaluated. Preparations of recombinant bispecific heterodimeric antibody were subject to SEC using a Superdex 200 preparative gel filtration column (2×80 ml) and a mobile phase comprising 50 mM HEPES, 0.75 M NaCl, 0.5 M arginine, 0.5 M proline, 2.2 M sorbitol, and 4 M urea at pH 7.2 at flow rates ranging from 0.02 ml/min to 0.2 ml/min (FIGS. 17A-17F). The results show that half antibodies are more efficiently separated from the fully assembled antibodies at slower flow rates with optimal separation occurring at flow rates of about 0.02 ml/min to about 0.06 ml/min (FIGS. 17A-17F).

Taken together, the experimental data described in this example show that use of a mobile phase comprising a chaotropic agent, a sugar alcohol, and amino acids in a SEC gel filtration column can efficiently separate half antibody contaminants and high molecular weight aggregates from fully assembled antibodies. This method provides a robust, one-step method to remove these problematic contaminants from recombinant antibody preparations, particularly multispecific heterodimeric antibody preparations.

All publications, patents, and patent applications discussed and cited herein are hereby incorporated by reference in their entireties. It is understood that the disclosed invention is not limited to the particular methodology, protocols and materials described as these can vary. It is also understood that the terminology used herein is for the purposes of describing particular embodiments only and is not intended to limit the scope of the appended claims.

Those skilled in the art will recognize, or be able to ascertain using no more than routine experimentation, many equivalents to the specific embodiments of the invention described herein. Such equivalents are intended to be encompassed by the following claims.

What is claimed:

1. A method for purifying a protein comprising an Fc region, comprising:
    contacting a solution comprising the protein and one or more impurities with a temperature-responsive protein A material at a temperature at which the protein binds to the material; and
    eluting the protein from the material at a temperature from about 1° C. to about 25° C. with an elution buffer having a pH of about 6.5 to about 7.5 and comprising a chaotropic agent, a sugar alcohol, an apolar amino acid, and a basic amino acid, wherein the protein is purified from one or more impurities in the solution.

2. The method of claim 1, wherein the chaotropic agent is urea, guanidinium chloride, sodium thiocyanate, potassium thiocyanate, or ammonium thiocyanate.

3. The method of claim 2, wherein the chaotropic agent is urea.

4. The method of claim 3, wherein the urea is present at a concentration of about 2 M to about 4.5 M.

5. The method of claim 4, wherein the urea is present at a concentration of about 4 M.

6. The method of claim 1, wherein the sugar alcohol is sorbitol, mannitol, xylitol, or glycerol.

7. The method of claim 1, wherein the sugar alcohol is sorbitol.

8. The method of claim 1, wherein the sugar alcohol is present at a concentration of about 1 M to about 4.5 M.

9. The method of claim 8, wherein the sugar alcohol is present at a concentration of about 2 M to about 2.5 M.

10. The method of claim 1, wherein the basic amino acid is histidine, lysine, ornithine, or arginine.

11. The method of claim 10, wherein the basic amino acid is arginine.

12. The method of claim 1, wherein the apolar amino acid is alanine, cysteine, glycine, isoleucine, leucine, methionine, phenylalanine, proline, tryptophan, or valine.

13. The method of claim 12, wherein the apolar amino acid is proline.

14. The method of claim 1, wherein the basic amino acid and/or the apolar amino acid is present at a concentration of about 0.25 M to about 1 M.

15. The method of claim 1, wherein the basic amino acid and/or the apolar amino acid is present at a concentration of about 0.5 M.

16. The method of claim 1, wherein the elution buffer further comprises a salt.

17. The method of claim 16, wherein the salt is present at a concentration of about 0.25 M to about 0.8 M.

18. The method of claim 16, wherein the salt is sodium chloride.

19. The method of claim 18, wherein the elution buffer comprises about 2 M to about 4.5 M urea, about 1 M to about 4.5 M sorbitol, about 0.25 M to about 1 M arginine, about 0.25 M to about 1 M proline, and about 0.25 M to about 0.8 M sodium chloride.

20. The method of claim 19, wherein the elution buffer comprises about 4 M urea, about 2.2 M sorbitol, about 0.5 M arginine, about 0.5 M proline, and about 0.75 M sodium chloride.

21. The method of claim 1, wherein the elution buffer has a pH of about 7.0 to about 7.4.

22. The method of claim 1, wherein eluting the protein from the material is performed at a temperature from about 1° C. to about 6° C.

23. The method of claim 1, wherein eluting the protein from the material is performed at a temperature from about 20° C. to about 25° C.

24. The method of claim 1, wherein the temperature-responsive protein A material is immobilized to a solid phase.

25. The method of claim 24, wherein the solid phase is a bead, a resin, a gel, a film, or a particle.

26. The method of claim 1, wherein contacting the solution with the material is performed at a temperature of about 10° C. or less.

27. The method of claim 26, wherein contacting the solution with the material is performed at a temperature of about 1° C. to about 6° C.

28. The method of claim 1, further comprising washing the material having the bound protein with one or more wash solutions prior to eluting the protein from the material.

29. The method of claim 28, wherein the one or more wash solutions comprises sodium chloride at a concentration of about 0.5 M to about 2 M.

30. The method of claim 1, wherein the protein comprising an Fc region is recombinantly produced in a mammalian cell.

31. The method of claim 30, wherein the mammalian cell is a Chinese Hamster Ovary cell.

32. The method of claim 1, wherein the protein comprising an Fc region is an antibody.

33. The method of claim 1, wherein the protein comprising an Fc region is an Fc fusion protein.

34. The method of claim 33, wherein the Fc fusion protein comprises at least one single chain Fv fragment.

35. The method of claim 1, wherein one or more impurities comprises host cell protein, host cell DNA, cell culture protein, or combinations thereof.

36. The method of claim 1, wherein the solution comprising the protein and one or more impurities is a harvest from a production bioreactor.

37. The method of claim 1, wherein the solution comprising the protein and one or more impurities is a cell culture supernatant.

38. The method of claim 1, wherein the solution comprising the protein and one or more impurities is a cell lysate.

39. The method of claim 1, wherein at least 70% of the Fc region-containing protein in the eluate from the material is in monomeric form.

40. The method of claim 1, wherein at least 80% of the Fc region-containing protein in the eluate from the material is in monomeric form.

41. The method of claim 1, wherein at least 90% of the Fc region-containing protein in the eluate from the material is in monomeric form.

42. The method of claim 1, further comprising subjecting the eluted Fc region-containing protein to one or more chromatography steps.

43. The method of claim 42, wherein said one or more chromatography steps is ion exchange chromatography, hydrophobic interaction chromatography, mixed mode chromatography, size exclusion chromatography, hydroxyapatite chromatography, metal affinity chromatography, or combinations thereof.

44. The method of claim 1, further comprising subjecting the eluted Fc region-containing protein to size exclusion chromatography using a mobile phase having a pH of about 6.5 to about 7.5 and comprising a chaotropic agent, a sugar alcohol, an apolar amino acid, and a basic amino acid.

45. A method for purifying a protein comprising an Fc region from a solution comprising the protein and one or more impurities, comprising:
adsorbing the protein to a temperature-responsive protein A material at a temperature at which the protein binds to the material; and
eluting the protein from the material at a temperature from about 1° C. to about 25° C. with an elution buffer having a pH of about 6.5 to about 7.5 and comprising a chaotropic agent and a sugar alcohol, wherein the molar concentration ratio of the chaotropic agent to sugar alcohol is about 0.4 to about 4.5.

46. The method of claim 45, wherein the molar concentration ratio of the chaotropic agent to sugar alcohol is about 1.5 to about 2.5.

47. The method of claim 45, wherein the molar concentration ratio of the chaotropic agent to sugar alcohol is about 1.8 to about 2.2.

48. The method of claim 45, wherein the molar concentration ratio of the chaotropic agent to sugar alcohol is about 0.5 to about 1.5.

49. The method of claim 45, wherein the chaotropic agent is urea, guanidinium chloride, sodium thiocyanate, potassium thiocyanate, or ammonium thiocyanate.

50. The method of claim 49, wherein the chaotropic agent is urea.

51. The method of claim 49, wherein the chaotropic agent is guanidinium chloride.

52. The method of claim 45, wherein the sugar alcohol is sorbitol, mannitol, xylitol, or glycerol.

53. The method of claim 52, wherein the sugar alcohol is sorbitol.

54. The method of claim 45, wherein the elution buffer further comprises one or more amino acids.

55. The method of claim 54, wherein the elution buffer comprises a basic amino acid and/or an apolar amino acid.

56. The method of claim 55, wherein the basic amino acid is histidine, lysine, ornithine, or arginine.

57. The method of claim 56, wherein the basic amino acid is arginine.

58. The method of claim 55, wherein the apolar amino acid is alanine, cysteine, glycine, isoleucine, leucine, methionine, phenylalanine, proline, tryptophan, or valine.

59. The method of claim 58, wherein the apolar amino acid is proline.

60. The method of claim 54, wherein the elution buffer comprises arginine and proline.

61. The method of claim 45, wherein the elution buffer further comprises a salt.

62. The method of claim 61, wherein the salt is sodium chloride.

63. The method of claim 45, wherein the elution buffer has a pH of about 7.0 to about 7.4.

64. The method of claim 1, wherein eluting the protein from the material is performed at a temperature from about 1° C. to about 6° C.

65. The method of claim 1, wherein eluting the protein from the material is performed at a temperature from about 20° C. to about 25° C.

66. The method of claim 45, wherein the temperature-responsive protein A material is immobilized to a solid phase.

67. The method of claim 66, wherein the solid phase is a bead, a resin, a gel, a film, or a particle.

68. The method of claim 45, wherein adsorbing the protein to the temperature-responsive protein A material is performed at a temperature of about 10° C. or less.

69. The method of claim 68, wherein adsorbing the protein to the temperature-responsive protein A material is performed at a temperature of about 1° C. to about 6° C.

70. The method of claim 45, further comprising washing the material having the bound protein with one or more wash solutions prior to eluting the protein from the material.

71. The method of claim 45, wherein the protein comprising an Fc region is recombinantly produced in a mammalian cell.

72. The method of claim 71, wherein the mammalian cell is a Chinese Hamster Ovary cell.

73. The method of claim 45, wherein the protein comprising an Fc region is an antibody.

74. The method of claim 45, wherein the protein comprising an Fc region is an Fc fusion protein.

75. The method of claim 74, wherein the Fc fusion protein comprises at least one single chain Fv fragment.

76. The method of claim 45, wherein the solution comprising the protein and one or more impurities is a harvest from a production bioreactor.

77. The method of claim 45, wherein the solution comprising the protein and one or more impurities is a cell culture supernatant.

78. The method of claim 45, wherein the solution comprising the protein and one or more impurities is a cell lysate.

79. The method of claim 45, wherein at least 70% of the Fc region-containing protein in the eluate from the material is in monomeric form.

80. The method of claim 45, wherein at least 80% of the Fc region-containing protein in the eluate from the material is in monomeric form.

81. The method of claim 45, wherein at least 90% of the Fc region-containing protein in the eluate from the material is in monomeric form.

82. The method of claim 45, further comprising subjecting the eluted Fc region-containing protein to one or more chromatography steps.

83. The method of claim 82, wherein said one or more chromatography steps is ion exchange chromatography, hydrophobic interaction chromatography, mixed mode chromatography, size exclusion chromatography, hydroxyapatite chromatography, metal affinity chromatography, or combinations thereof.

84. The method of claim 45, further comprising subjecting the eluted Fc region-containing protein to size exclusion chromatography using a mobile phase having a pH of about 6.5 to about 7.5 and comprising a chaotropic agent, a sugar alcohol, an apolar amino acid, and a basic amino acid.

85. A method for purifying a protein comprising an Fc region, comprising:
contacting a solution comprising the protein and one or more impurities with a temperature-responsive protein A material at a temperature at which the protein binds to the material; and
eluting the protein from the material at a temperature below about 35° C. with an elution buffer having a pH of about 6.5 to about 7.5 and comprising 2 M to about 4.5 M urea, about 1 M to about 4.5 M sorbitol, about 0.25 M to about 1 M arginine, about 0.25 M to about 1 M proline, and 0.25 M to about 0.8 M sodium chloride,
wherein the protein is purified from one or more impurities in the solution.

* * * * *